US012594253B2

(12) United States Patent
Rodnina-Wintermeyer et al.

(10) Patent No.: US 12,594,253 B2
(45) Date of Patent: Apr. 7, 2026

(54) HIV INHIBITORS

(71) Applicant: Max-Planck-Gesellschaft zur Förderung der Wissenschaften e.V., Munich (DE)

(72) Inventors: Marina V. Rodnina-Wintermeyer, Gottingen (DE); Natalia Korniy, Gottingen (DE); Ekaterina Samatova, Gottingen (DE); Frank Peske, Hannover (DE)

(73) Assignee: MAX-PLANCK-GESELLSCHAFT ZUR FÖRDERUNGDER WISSENSCHAFTEN E.V., Munich (DE)

( * ) Notice: Subject to any disclaimer, the term of this patent is extended or adjusted under 35 U.S.C. 154(b) by 1215 days.

(21) Appl. No.: 17/262,705

(22) PCT Filed: Jul. 24, 2019

(86) PCT No.: PCT/EP2019/069896
§ 371 (c)(1),
(2) Date: Jan. 22, 2021

(87) PCT Pub. No.: WO2020/020935
PCT Pub. Date: Jan. 30, 2020

(65) Prior Publication Data
US 2021/0251930 A1     Aug. 19, 2021

(30) Foreign Application Priority Data
Jul. 25, 2018     (EP) .................................... 18185487

(51) Int. Cl.
*A61K 31/198*     (2006.01)
*A61K 47/54*     (2017.01)
*A61P 31/18*     (2006.01)

(52) U.S. Cl.
CPC .......... *A61K 31/198* (2013.01); *A61K 47/549* (2017.08); *A61P 31/18* (2018.01)

(58) Field of Classification Search
CPC ............... A61K 31/198; A61K 47/549; A61K 31/7105; A61K 45/06; A61P 31/18
See application file for complete search history.

(56) References Cited

U.S. PATENT DOCUMENTS

| | | |
|---|---|---|
| 3,687,808 A | 8/1972 | Merigan, Jr. et al. |
| 2011/0306653 A1 | 12/2011 | Hirao et al. |
| 2017/0292126 A1* | 10/2017 | Anderson ............... A61P 25/00 |

FOREIGN PATENT DOCUMENTS

| | | |
|---|---|---|
| WO | 2012006551 A2 | 1/2012 |
| WO | 2017152809 A1 | 9/2017 |

OTHER PUBLICATIONS

Kirino, Yohei, et al. "Acquisition of the wobble modification in mitochondrial tRNALeu (CUN) bearing the G12300A mutation suppresses the MELAS molecular defect." Human molecular genetics 15.6 (2006): 897-904. (Year: 2006).*

Dulude, Dominic, et al. "Decreasing the frameshift efficiency translates into an equivalent reduction of the replication of the human immunodeficiency virus type 1." Virology 345.1 (2006): 127-136. (Year: 2006).*

Yelverton, Elizabeth, et al. "The function of a ribosomal frameshifting signal from human immunodeficiency virus-1 in *Escherichia coli*." Molecular microbiology 11.2 (1994): 303-313. (Year: 1994).*

Dulude et al., "Decreasing the frameshift efficiency translates into an equivalent reduction of the replication of the human immunodeficiency virus type 1", VIROLOGY, 2006, pp. 127-136, vol. 345.

Brierley, "Review article Ribosomal frameshifting on viral RNAs", Journal of General Virology, 1995, pp. 1885-1892, vol. 76.

Elmen et al., "Locked nucleic acid (LNA) mediated improvements in siRNA stability and functionality", Nucleic Acids Research, 2005, pp. 439-447, vol. 33(1).

Mook et al., "Evaluation of locked nucleic acid-modified small interfering RNA in vitro and in vivo", Mol Cancer Ther, 2007, pp. 833-843, vol. 6(3).

Grunweller et al., "Comparison of different antisense strategies in mammalian cells using locked nucleic acids, 2'-O-methyl RNA, phosphorothioates and small interfering RNA", Nucleic Acids Research, 2003, pp. 3185-3193, vol. 31(12).

Savelsbergh et al., "An Elongation Factor G-Induced Ribosome Rearrangement Precedes IRNA-mRNA Translocation", Molecular Cell, Jun. 2003, pp. 1517-1523, vol. 11.

Florin et al., "An antimicrobial peptide that inhibits translation by trapping release factors on the ribosome", Nat Struct Mol Biol. Sep. 2017, pp. 752-757, vol. 24(9).

Mittelstaet et al., "A Kinetic Safety Gate Controlling the Delivery of Unnatural Amino Acids to the Ribosome", Journal of the American Chemical Society, Sep. 30, 2013, pp. 17031-17038, vol. 135.

Rodnina et al., "Thiostrepton inhibits the turnover but not the GTPase of elongation factor G on the ribosome", Proc. Natl. Acad. Sci. USA, Aug. 1999, pp. 9586-9590, vol. 96.

Milligan et al., "Oligoribonucleotide synthesis using T7 RNA polymerase and synthetic DNA templates", Nucleic Acids Research, 1987, pp. 8783-8798, vol. 15(21).

Tabor et al., "A bacteriophage T7 RNA polymerase/promoter system for controlled exclusive expression of specific genes", Proc. Natl. Acad. Sci. USA, Feb. 1985, pp. 1074-1078, vol. 82.

Mathew et al., "The Highly Conserved Codon following the Slippery Sequence Supports—1 Frameshift Efficiency at the HIV-1 Frameshift Site", PLOS One, Mar. 25, 2015, pp. 1-24, e0122176.

Korniy et al., "Modulation of HIV-1 Gag/Gag-Pol frameshifting by tRNA abundance", Nucleic Acids Research, 2019, pp. 5210-5222, vol. 47(10).

(Continued)

*Primary Examiner* — Jennifer Dunston
*Assistant Examiner* — John Charles McKillop
(74) *Attorney, Agent, or Firm* — Pillsbury Winthrop Shaw Pittman, LLP

(57) ABSTRACT

The present invention relates to a compound comprising of the nucleotide sequence UAA or TAA and a binding site for the covalent attachment of leucine (Leu), wherein said compound is recognized by a ribosome, for use in medicine.

Figures 2A, 2B, 2C, 2D, 2E:
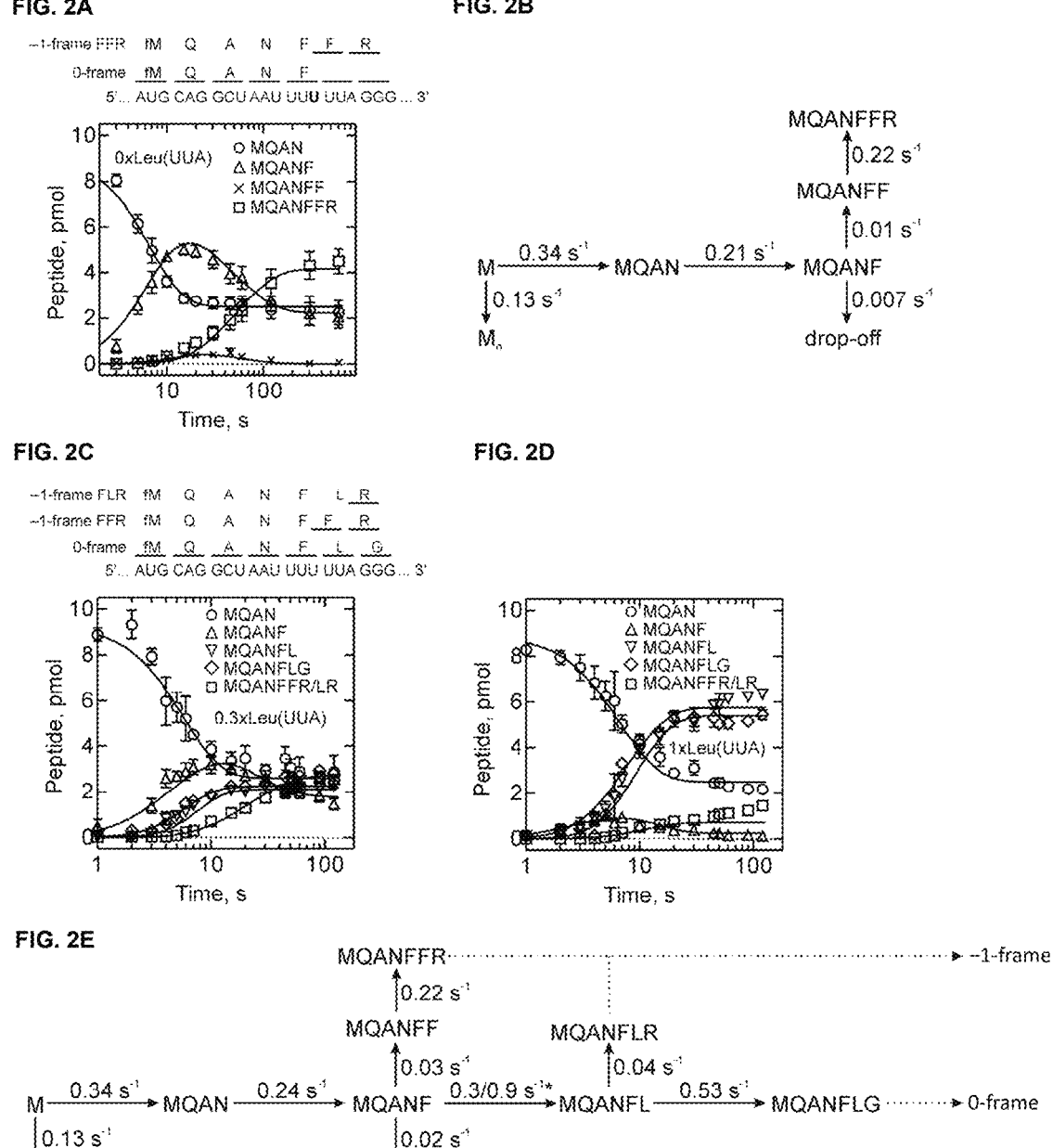

3 Claims, 6 Drawing Sheets
Specification includes a Sequence Listing.

(56) References Cited

OTHER PUBLICATIONS

Caliskan et al., "Conditional Switch between Frameshifting Regimes upon Translation of dnaX mRNA", Molecular Cell, 2017, pp. 558-567, vol. 66.

Yelverton et al., "The function of a ribosomal frameshifting signal from human immunodeficiency virus-1 in *Escherichia coli*", Molecular Microbiology, 1994, pp. 303-313, vol. 11(3).

Dittmar et al., "Tissue-Specific Differences in Human Transfer RNA Expression", PLOS Genetics, Dec. 22, 2006, 2107-2115, vol. 2(12), e221.

Sharp et al., "Codon usage patterns in *Escherichia coli, Bacillus subtilis, Saccharomyces cerevisiae, Schizosaccharomyces pombe, Drosophila melanogaster* and *Homo sapiens*; a review of the considerable within-species diversity", Nucleic Acids Research, 1988, pp. 8207-8211, vol. 16(17).

Van Weringh et al., "HIV-1 modulates the tRNA pool to improve translation efficiency", Mol. Biol. Evol., Jan. 7, 2011, pp. 1827-1834, vol. 28(6).

Buhr et al., "Synonymous Codons Direct Cotranslational Folding toward Different Protein Conformations", Cell, Feb. 4, 2016, pp. 341-351, vol. 61.

Ingolia et al., "Ribosome Profiling of Mouse Embryonic Stem Cells Reveals the Complexity and Dynamics of Mammalian Proteomes", Cell, Nov. 11, 2011, pp. 789-802, vol. 147.

Firth et al., "Discovery of frameshifting in Alphavirus 6K resolves a 20-year enigma", Virology Journal, Sep. 26, 2008, pp. 1-19, vol. 5 (108).

Cassan et al., "Translational frameshifting at the gag-pol junction of human immunodeficiency virus type 1 is not increased in infected T-lymphoid cells", Journal of Virology, Mar. 1994, pp. 1501-1508. vol. 68(3).

Plant et al., "Comparative study of the effects of heptameric slippery site composition on—1 frameshifting among different eukaryotic systems", RNA, 2006, pp. 666-673, vol. 12.

Parkin et al., "Human immunodeficiency virus type 1 gag-pol frameshifting is dependent on downstream mRNA secondary structure: demonstration by expression in vivo", Journal of Virology, Aug. 1992, pp. 5147-5151, vol. 66(8).

Yacoubi et al., "Biosynthesis and Function of Posttranscriptional Modifications of Transfer RNAs", Annual Review of Genetics, Aug. 2012, pp. 69-95, vol. 46.

Mullis, KB, "Target amplification for DNA analysis by the polymerase chain reaction", Annales de Biologie Clinique, Dec. 31, 1989, pp. 579-582, vol. 48(8).

Patent Cooperation Treaty, International Search Report and Written Opinion issued in PCT/EP2016/069896, Nov. 13, 2019, pp. 1-12.

Caliskan et al., "Programmed —1 Frameshifting by Kinetic Partitioning during Impeded Translocation", Cell, Jun. 19, 2014, pp. 1619-1631, vol. 157.

Caliskan et al., "Conditional Switch between Frameshifting Regimes upon Translation of dnaX mRNA", Molecular Cell, May 18, 2017, pp. 558-567, vol. 66.

Jones et al., "Regulation of membrane protein degradation by starvation-response pathways", Traffic, Mar. 2012, pp. 468-482, vol. 13(3).

Korniy et al., "Modulation of HIV-1 Gag/Gag-Pol frameshifting by tRNA abundance" Nucleic Acids Research, Apr. 10, 2019, pp. 5210-5222, vol. 47(10).

Sheen et al., "Defective regulation of autophagy upon leucine deprivation reveals a targetable liability of human melanoma cells in vitro and in vivo", Cancer Cell, May 17, 2011, pp. 613-628, vol. 19(5).

Xiao et al., "Leucine Deprivation Increases Hepatic Insulin Sensitivity via GCN2/mTOR/S6K1 and AMPK Pathways", Diabetes, Mar. 2011, pp. 746-756, vol. 60.

Averous et al., "GCN2 contributes to mTORC1 inhibition by leucine deprivation through an ATF4 independent mechanism", Scientific Reports, Jun. 14, 2016, pp. 1-10.

* cited by examiner

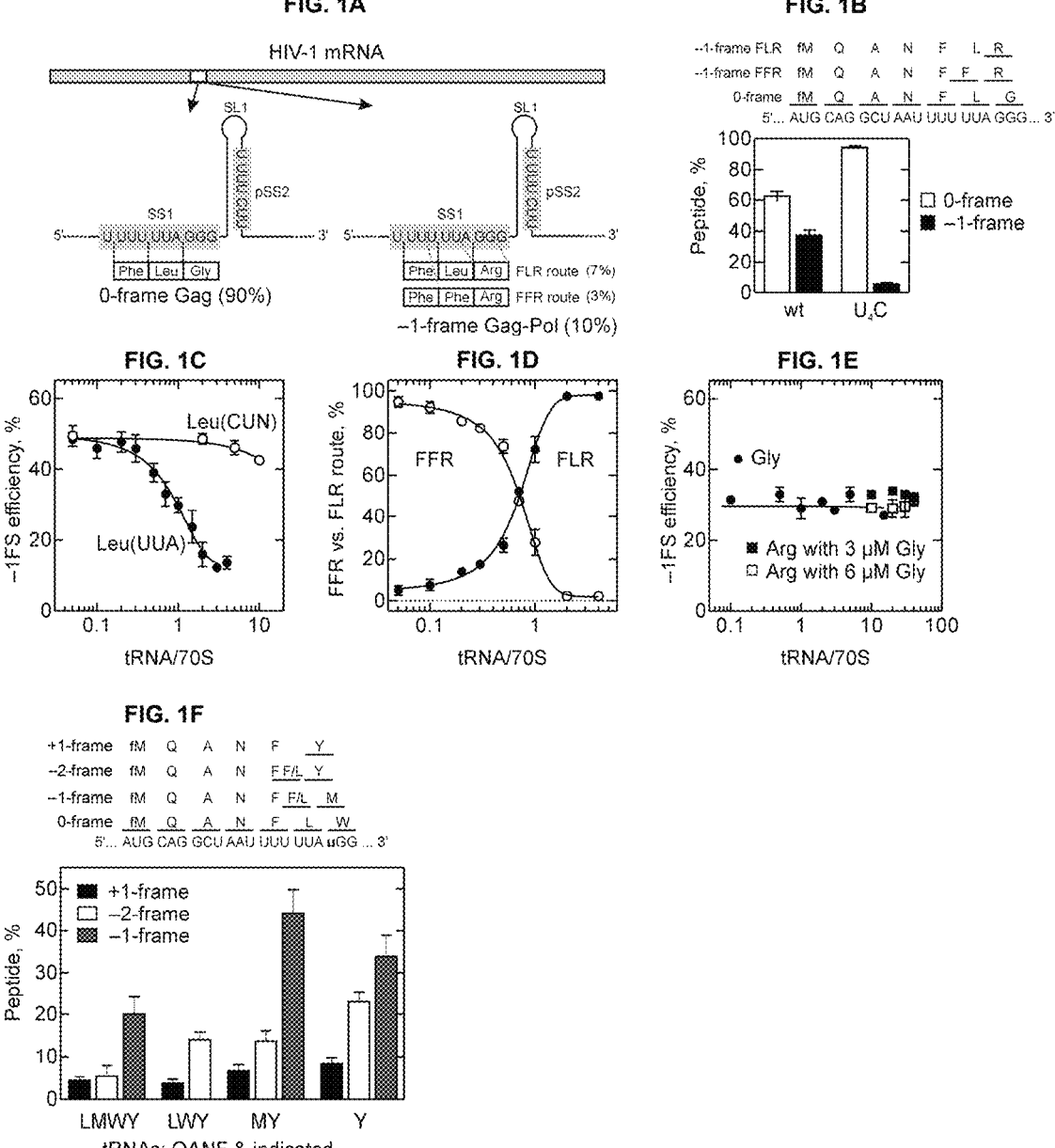

SL1 pSS2

SS1          pSL2

5'------AUGAAA GAU UGU ACU GAG AGA CAG GCU AAU UUU UUA GGG ------- 3'
└----► 0-frame 52 aa
└----► –1-frame 120 aa
└----► –2-frame 120 aa frame markers Time: 2"  4"  7"  10"  15"  20"  30"  45"  1'  2'  3'  5'  6'  7'  10'  25'  –1  0

←–1-frame

←0-frame

–1, wt mRNA
–1, no-stop
–2, no-stop

FS efficiency, %

Time, min wt mRNA

–1FS efficiency, % tRNA/70S

–1FS efficiency, %

SS1  U UUU UUA  U UUU UUc  U UUU cUg  c UUc gUA

FIG. 4

HIV INHIBITORS

CROSS-REFERENCE TO RELATED APPLICATIONS

This application is a Section 371 National Stage Application of International Application PCT/EP2019/069896, filed on Jul. 4, 2019, entitled "HIV INHIBITORS", which claims priority to European Patent Application 18185487.8, filed on Jul. 25, 2018, entitled "RNAYLATION". The disclosure of the afore-listed patent filings are incorporated herein by reference in their entirety, including all text, tables and drawings.

SEQUENCE LISTING

This application contains a Sequence Listing that has been submitted electronically in ASCII format and is hereby incorporated by reference in its entirety. The ASCII copy, created on Jul. 8, 2024, is named "009848-0516526_ST25.txt" and is 22,374 bytes in size.

The present invention relates to a compound comprising of the nucleotide sequence UAA or TAA and a binding site for the covalent attachment of leucine (Leu), wherein said compound is recognized by a ribosome, for use in medicine.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Many viruses use programmed ribosome frameshifting to increase genome-coding capacity and to regulate stoichiometric ratio between viral proteins (Jacks et al, (1988). Cell 55, 447-458). Two major HIV-1 genes, gag and pol, overlap by 205 nt. Synthesis of the Gag-Pol polyprotein requires −1 ribosome frameshifting (−1FS) (Jacks et al, (1988). Cell 55, 447-458). The ratio between Gag and Gag-Pol is crucial for virus propagation and its dysregulation is detrimental for replication, particle formation, and infectivity of HIV-1 (Karacostas et al. (1993). Virology 193, 661-671). The efficiency of gag-pol −1FS in human cells is about 10% ranging from 2% to 11% depending on the reporter (Cassan et al. (1994). J Virol 68, 1501-1508; Plant and Dinman, (2006). RNA 12, 666-673)). This −1FS efficiency has been recapitulated in vivo or in vitro with the help of mammalian, yeast or *Escherichia coli* translation extracts (Bidou et al. (1997). RNA 3, 1153-1158; Brunelle et al. (1999). Nucleic Acids Res 27, 4783-4874; Jacks et al. (1988). Nature 331, 280-283; Parkin et al. (1992). J Virol 66, 5147-5151; Plant and Dinman (2006). RNA 12, 666-673; Weiss et al. (1989). New Biol 1, 159-169; Yelverton et al. (1994). Mol Microbiol 11, 303-313).

−1FS is governed by two cis-acting elements, the slippery site (SS1) $U_1$ $UUU_4$ $UUA_7$ encoding Phe and Leu in 0-frame (Jacks et al. (1988). Nature 331, 280-283) and a stem-loop (SL1) structure (FIG. 1A). The slippery sequence gives rise to two frameshifting products, one that contains the 0-frame peptide Phe-Leu followed by the −1-frame sequence (FLR product; FIG. 1A,B), and another with a second Phe incorporated instead of Leu (FFR product); the ratio of the two −1FS products is about 70% to 30% (Jacks et al. (1988). Nature 331, 280-283).

While a variety of HIV therapeutics is available, art-established therapy options suffer from several shortcomings which include the development of resistance and adverse effects. As such, there is an ongoing need for novel and improved treatment options for retroviral infections.

Therefore, the technical problem underlying the present invention can be seen in the provision of improved means and methods of treating AIDS and HIV infection. This technical problem is solved by the subject-matter of the enclosed claims.

Accordingly, in a first aspect, the present invention relates to a compound comprising of the nucleotide sequence UAA or TAA and a binding site for the covalent attachment of leucine (Leu), wherein said compound is recognized by a ribosome, for use in medicine.

The term "compound" refers to one or a plurality of molecules (including a macroscopic quantity) meeting the requirements set forth above, wherein said nucleotide sequence and said binding site are comprised within the same molecule, i.e. they are directly or indirectly covalently connected to each other.

The compound of the invention can be seen as a carrier molecule. It comprises a binding site for the amino acid leucine, more specifically L-leucine, which is one of the 20 proteinogenic amino acids. Said binding site may be free or occupied with leucine.

Owing to the degeneracy of the genetic code, for most of the proteinogenic amino acids more than one codon is available. In case of leucine, the DNA codons are: CTT, CTC, CTA, CTG, TTA and TTG. DNA is transcribed into mRNA, and the message carried by the mRNA is translated to polypeptides by the ribosomal machinery. The ribosome employs carrier molecules which are known as transfer RNAs (tRNAs). One of the transfer RNAs which carry leucine has an anticodon which is complementary to the TTA DNA codon (which corresponds to UUA at the mRNA level). Said complementary anticodon has the sequence UAA. As such, the compound in accordance with the first aspect implements two key features of a particular leucyl-tRNA.

Apart from the two structural features recited above, i.e. said nucleotide sequence and said binding site, the compound in accordance with the first aspect is not particularly limited, provided that it is recognized by a ribosome.

Recognition by a ribosome has the following implications in accordance with this disclosure: ribosomes have tRNA binding sites. Furthermore, ribosomes catalyze the formation of a peptide bond at the end of a growing polypeptide chain; see, e.g., Stryer, Biochemistry; Freeman, ISBN 1319153933. Recognition of a compound of the invention by a ribosome means that said compound is processed by a ribosome in accordance with these two functions of the ribosome. First, the compound occupies a tRNA binding site of said ribosome, and secondly, the amino acid Leu, to the extent present, is amenable for coupling to a growing polypeptide chain.

Said ribosome is preferably a eukaryotic ribosome, more preferably a mammalian ribosome, such as a ribosome of a primate, and most preferably a human ribosome.

Said binding site is not particularly limited. Having said that, and in particular in those embodiments where said nucleotide sequence is embedded in a longer polynucleotide sequence, a terminus of said polynucleotide sequence may constitute said binding site. It is particularly preferred that the 3' oxygen on the ribose or desoxyribose of the 3' end of said polynucleotide is connected via an ester bond to the carboxy terminus of said leucine.

Whether the requirement of recognition by a ribosome is fulfilled by a compound comprising said nucleotide sequence and said binding site can be tested, for example, by an assay for polypeptide chain extension (see, e.g., Zaher and Green (2014) Methods Enzymol. 539, 3-15.

Preferably, said nucleotide sequence is a ribonucleotide sequence. Preferred is UAA.

Preferred is that the mentioned polynucleotide is a polyribonucleotide. Preferred lengths of said polynucleotide are between 50 and 100 such as between 70 and 95 nucleotides such as 86 nucleotides.

In the context of the binding site, it is preferred that said 3' terminal nucleotide is A.

Particularly preferred is that said A is preceded by CC, such that the 3' terminal sequence comprising said binding site is CCA. In other words, in a preferred embodiment said binding site is the sequence CCA. Preferably, said 3' terminal nucleotide or said 3' terminal sequence is an overhang or is comprised in an overhang.

The present inventors surprisingly discovered that variations in the concentration of the compound in accordance with the first aspect severely affects the frameshift efficiency in the region of the HIV genome discussed herein above. Since the degree of frameshifting controls the ratio of the gag gene product to the gag-pol gene product, interfering with frameshifting efficiency is a means to modulate virus propagation. To explain further, administration of a compound in accordance with the first aspect leads to a reduction in frameshift efficiency, which in turn causes a misbalanced gag to gag-pol ratio, which misbalance abrogates virus propagation, in particular virus assembly and infectivity.

Said interference with HIV replication does not negatively affect the expression of the genes in the cells of the individual to whom said compound is to be administered.

A further advantage of the present invention is the universality of the UAA codon occurring at the slippery site. Owing to its universal conservation across taxonomic categories, specific resistance mechanisms are less likely to emerge, in particular when compared to other anti-HIV drugs that target less conserved structures or targets.

Said individual is preferably a mammal, more preferably a primate, and most preferably a human.

In a preferred embodiment, said compound comprises said Leu, more specifically L-Leu.

In a further preferred embodiment, (a) said compound is recognized by an aminoacyl tRNA synthetase and, to the extent said compound does not comprise said Leu, said compound is capable of being charged with said Leu by said synthetase; (b) said ribonucleotide sequence is capable of base pairing with a nucleic acid, preferably an mRNA, said nucleic acid comprising the sequence UUA or TTA; and/or (c) said Leu is present and available for attachment to a growing polypeptide chain by said ribosome.

Item (a) of this embodiment is only of relevance for compounds in accordance with the first aspect which do not comprise leucine. Such compound may nevertheless be administered for therapeutic purposes, wherein charging with leucine is effected by an endogenous amino acyl tRNA synthetase. Also in this context, Leu is preferably L-Leu.

Item (b) explicitly spells out a property which is generally inherent to nucleotide sequences. In particular, it expresses the requirement that the nucleotide sequence is accordance with the first aspect (UAA or TAA) assumes a conformation or is capable of assuming a conformation which allows base-pairing with a complementary sequence, said complementary sequence being the tri-nucleotide sequence UUA or TTA. Preferably, said nucleotide sequence is not base-paired within said compound. More preferably, said nucleotide sequence (UAA or TAA) is comprised in a loop of a stem-loop, wherein preferably the stem in said stem-loop comprises a single-stranded end, said single-stranded end comprising said binding site. Said single-stranded end is preferably the 3' end. Said single-stranded end is also referred to as an overhang in this disclosure. A particularly preferred length of said single-stranded end or overhang is four nucleotides. Less preferred lengths include 1, 2, 3, 5, 6, 7, 9 and 10 nucleotides.

Given that the compound in accordance with the first aspect is recognized by a ribosome, this implies that Leu, when comprised in said compound, upon binding of said compound to said ribosome, is available in accordance with (c) for attachment to the growing polypeptide chain via the peptidyl transferase activity of the ribosome.

In a second aspect, the present invention provides the compound in accordance with the first aspect for use in a method of treating, ameliorating or preventing an infection with HIV virus, with SIV virus, with an Alphavirus and/or AIDS. This aspect relates to therapeutic and/or prophylactic applications.

To explain further, the underlying principle of the invention, i.e., a UUA codon at the site amenable to frameshifting is not confined to immunodeficiency viruses. Viruses belonging to the genus Alphavirus (which in turn belongs to the family Togaviridae) also comprise such sequences. Examples of *Alphaviruses* in accordance with the present invention are seal louse virus (SELV), Middelberg virus (MIDV), Venezuelan equine encephalitis virus (VEEV), Ndumu virus (NDUV), Sindbis virus (SINV), Barmah forest virus (BFV), sleeping disease virus (SDV), Eastern equine encephalitis virus (EEEV), and Semliki forest virus (SFV).

Human immunodeficiency virus (HIV) is an enveloped virus belonging to the family Retroviridae and to the genus *Lentivirus*. An untreated infection with HIV generally leads to a disease referred to as acquired immunodeficiency syndrome (AIDS). The genome of HIV encodes nine genes, which are known as gag, pol, vif, vpr, vpu, tat, ref, env and nef. Gag, pol and env are the canonical retroviral genes. The remainder of the above mentioned genes is also referred to as accessory genes. Translation of the viral genome also yields a gag-pol polyprotein. As noted above, the quantitative ratio between the gag and the gag-pol product is crucial for viability of the virus.

Preferably, said HIV is HIV-1. It may also be HIV-2.

In a preferred embodiment of first and second aspect, said compound comprises or consists of a polynucleotide such as a polyribonucleotide, said polynucleotide comprising said binding site, said polynucleotide preferably being a $tRNA^{Leu(UAA)}$ more preferably a mammalian $tRNA^{Leu(UAA)}$, and $tRNA^{Leu(UAA)}$ of a primate, or a human $tRNA^{Leu(UAA)}$. The abbreviation "tRNA" designates, as established in the art, a transfer RNA; see, e.g., El Yacoubi et al. (2012) Annu Rev Genet 46, 69-95. The superscript "Leu(UAA)" indicates that the transfer RNA is charged or may be charged with L-leucine, wherein the anticodon sequence is UAA.

The abbreviation $tRNA^{Leu}$ refers to a genus of tRNA molecules which all carry Leu or can be charged therewith, and the anticodon is complementary to one of CTT, CTC, CTA, CTG, TTA and TTG. The individual tRNAs within said genus are characterized by defined anticodon. tRNAs with a defined anticodon are also referred to as "isoacceptors" in the art.

In a particularly preferred embodiment said polynucleotide comprises or consists of the sequence of SEQ ID NO: 1 or 2.

Figure 4:
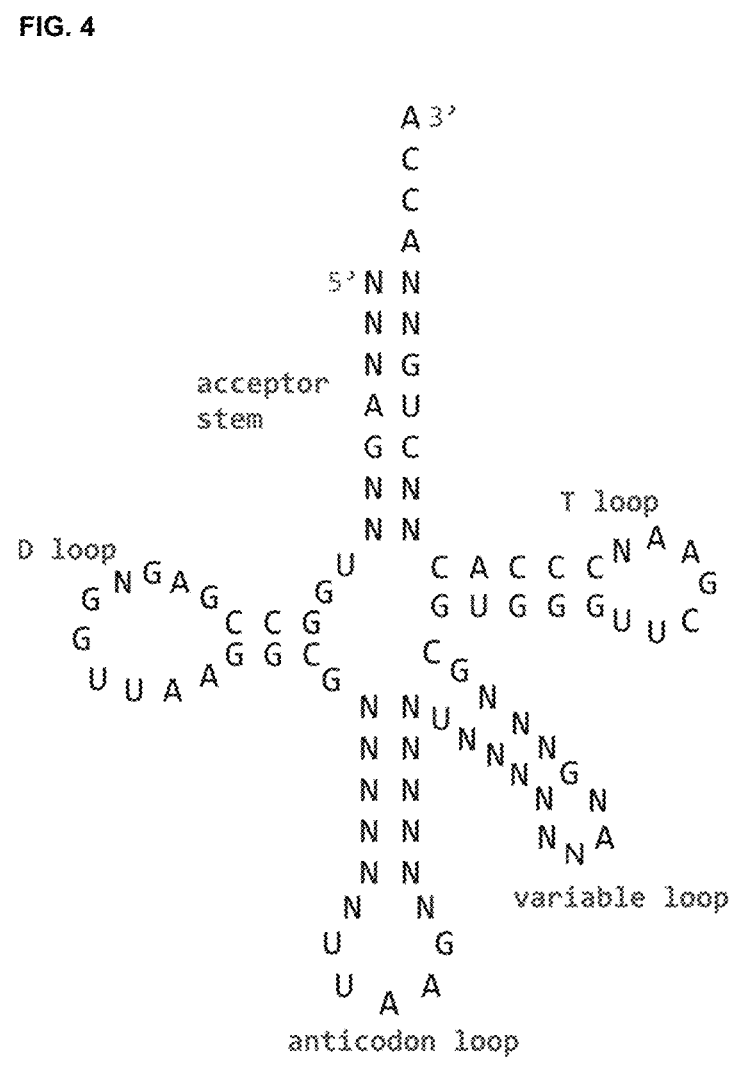

It is an inherent property of the sequence of SEQ ID NO: 1 to assume a defined secondary structure, which in turn is related to a defined three dimensional structure. The secondary structure of the sequence of SEQ ID NO: 1 is shown in FIG. 4.

SEQ ID NO: 1 has the following sequence:

```
NNNAGNNUGGCCGAGNGGUUAAGGCGNNNNNNNUUAAGNNNNNNNUNNNNN
NANGNNNGCGUGGGUUCGAANCCCACNNCUGNNACCA
```

This aspect of the invention relates to those tRNA$^{Leu(UAA)}$ molecules which do not occur in nature. It is understood that derivatives in accordance with the third aspect are recognized by a ribosome, preferably in the sense defined above. Human tRNA$^{Leu(UAA)}$ molecules have one of the sequences of SEQ ID NOs: 3 to 11, SEQ ID NO: 3 occurring most frequently.

The sequences of SEQ ID NOs: 3 to 11 are also reproduced below. Each of the sequences defines a preferred human wild-type tRNA$^{Leu(UAA)}$, SEQ ID NO: 3 being particularly preferred.

```
>Homo_sapiens_tRNA-Leu-TAA-1-1 (chr6.trna81-LeuTAA) chr6:144537684-144537766 (+)
Leu (TAA) 83 bp Sc: 92.1
ACCAGGATGGCCGAGTGGTTAAGGGGTTGGACTTAAGATCCAATGGACATATGTCCGC
GTGGGTTCGAACCCCACTCCTGGTA >Homo_sapiens_tRNA-Leu-TAA-2-1 (chr6.trna135-LeuTAA) chr6:27688898-27688980 (-)
Leu (TAA) 83 bp Sc: 85.0
ACCGGGATGGCCGAGTGGTTAAGGCGTTGGACTTAAGATCCAATGGGCTGGTGCCCGC
GTGGGTTCGAACCCCACTCTCGGTA >Homo_sapiens_tRNA-Leu-TAA-3-1 (chr11.trna4-LeuTAA) chr11:59319228-59319310 (+)
Leu (TAA) 83 bp Sc: 89.3
ACCAGAATGGCCGAGTGGTTAAGGCGTTGGACTTAAGATCCAATGGATTCATATCCGCG
TGGGTTCGAACCCCACTTCTGGTA >Homo_sapiens_tRNA-Leu-TAA-4-1 (chr6.trna156-LeuTAA) chr6:27198334-27198416 (-)
Leu (TAA) 83 bp Sc: 83.3
ACCGGGATGGCTGAGTGGTTAAGGCGTTGGACTTAAGATCCAATGGACAGGTGTCCGC
GTGGGTTCGAGCCCCACTCCCGGTA >Homo_sapiens_tRNA-Leu-TAA-5-1 (chr6.trna79-LeuTAA) chr6:69914378-69914460 (+)
Leu (TAA) 83 bp Sc: 37.2
ACTCATTTGGCTGAGTGGTTAAGGCATTGGACTTAAGATCCAATGGAGTAGTGGCTGTG
TGGGTTTAAACCCCACTACTGGTA >Homo_sapiens_tRNA-Leu-TAA-chr1-9 (chr1.trna9-LeuTAA) chr1:55839111-55839179 (+)
Leu (TAA) 69 bp Sc: 27.3
GAGAAAGTCATCGTAGTTACGAAGTTGGCTTAAACCCAGTTTTGGGAGGTTCAATTCCTT
CCTTTCTCT >Homo_sapiens_tRNA-Leu-TAA-chr11-12 (chr11.trna12-LeuTAA) chr11:113432995-
113433078 (-) Leu (TAA) 84 bp Sc: 50.7
ACCAGGATGGCCAAGTAGTTAAAGGCACTGGACTTAAGAGCCAATGGACATATGTCTGT
GTGGGTTTGAACCCCACTCCTGGTG >Homo_sapiens_nmt-tRNA-Leu-TAA-1-1 (chr4.trna2-LeuTAA) chr4:156384978-156385052
(-) Leu (TAA) 75 bp Sc: 55.7
GTTAAGATGGCAGAGCCTGGTAATTGCATAAAACTTAAAATTTTATAATCAGAGGTTCAA
CTCCTCTTCTTAACA >Homo_sapiens_nmt-tRNA-Leu-TAA-4-1 (chrX.trna2-LeuTAA) chrX:55207755-55207829 (-)
Leu (TAA) 75 bp Sc: 30.0
GTTAAGATGGCAGAGCCCGGCAATTGCATAAGACTTAAAACTTTATAATCAGAGGTTCAA
CTCCTCTCATTAACA
```

SEQ ID NO: 2 has the following sequence:

```
ACCAGGAUGGCCGAGUGGUUAAGGCGUUGGACUUAAGAUCCAAUGGACA
UAUGUCCGCGUGGGUUCGAACCCCACUCCUGGUACCA
```

In a third aspect, the present invention provides a tRNA$^{Leu(UAA)}$ derivative which (a) differs from any wild-type tRNA$^{Leu(UAA)}$, preferably from any human wild-type tRNA$^{Leu(UAA)}$ by at least one mutation of the base sequence; (b) comprises at least one modification, preferably selected from a modification of a ribose and/or of a phosphate; (c) comprises at least one modification that increases stability in serum and/or in a cell; and/or (d) comprises at least one modification that increases cellular uptake.

Preferred mutations in accordance with item (a) are mutations in the stem connected to the anticodon loop, the stem connected to the variable loop, and in the acceptor stem. Reference is made to FIG. 4, where variable positions are indicated by N. It is understood that derivatives in accordance with item (a) may fulfil one or both functional requirements in accordance with items (c) and (d) of the third aspect of the invention. Preferred numbers of mutations in accordance with item (a) are 1, 2, 3, 4, 5, 6, 9, 10, 15, 20, 25, 30, 35 or 40 mutations. Preferred mutations are point mutations. Preferred point mutations are substitutions. As noted above, when substitutions occur at locations where N base pairs with an N, it is understood that base pairing is preferably maintained when a mutation occurs. The replacement of one base pair at an N—N site with another base pair counts as two point mutations in accordance with the present disclosure.

Mutations in accordance with (a) can be determined using art-established approaches. For example, this can be done using random libraries and a selection screen. In particular, constructs are prepared where one or more (such as 2, 3, 4, 5, 6, 7, 8, 9, or 10) positions are varied, such that the effects of A, C, G, and U at the tested position(s) is evaluated. The remaining positions are not changed in a given assay. The actual testing involves in vitro and/or in vivo tests for function. These tests are preferably performed under conditions where a molecule known to be active performs its normal function. Subsequently, active mutants are sequenced.

Deviant from item (a), which relates to replacements of one or more naturally occurring nucleotides within said derivates with one or more different naturally occurring nucleotides, item (b) defines modifications, which modifications do not occur in nature. Non-naturally occurring modifications comprise modifications which as such do not occur in nature as well as modifications which do occur naturally occurring tRNAs, but not at the given position under consideration within said tRNA derivative. Similar to item (a), it applies also to item (b) that those modifications which are defined in structural terms in accordance with item (b) may furthermore meet one or both functional requirements (c) and (d).

Preferred numbers of modifications in accordance with item (b) are 1, 2, 3, 4, 5, 6, 9, 10, 15, 20, 25, 30, 35 or 40 modifications.

It is of note that a modification in accordance with item (a) actually may obviate the necessity for chemical modifications in accordance with item (b).

Changes in accordance with items (a) and (b) may furthermore increase the tRNA amino acylation efficiency and/or the stability of the codon-anticodon interaction.

It is known that tRNA molecules, upon transcription, undergo a number of post-transcriptional modifications, generally catalyzed by cellular enzymes, which ensure or enhance function of the tRNA. These modifications are described, for example, in El Yacoubi et al. (2012) Annu Rev Genet 46, 69-95. The notion of derivatives in accordance with the third aspect does not embrace these post-transcriptional modifications. In other words, said at least one modification is a chemical or non-natural modification.

In addition, there is no requirement to provide compounds in accordance with first and second aspect or derivatives in accordance with third aspect which comprise these naturally occurring post-transcriptional modifications. This is the case because in their absence, these modifications will be introduced inside the cell upon administration of said compound or derivative to a cell.

Said post-transcriptional modifications in many instances affect bases. Typical modifications are given in Table 1 below. One, two, three, four, five or more such as all of the modifications given in Table 1 may be present.

TABLE 1

| Modifications of tRNAs of the invention. | |
| --- | --- |
| Modification | Position in SEQ ID NOs: 1 and 2 |
| N2-methylguanosine | 10 |
| N4-acetylcytidine | 12 |
| dihydrouridine | 16 |
| dihydrouridine | 19 |

TABLE 1-continued

| Modifications of tRNAs of the invention. | |
| --- | --- |
| Modification | Position in SEQ ID NOs: 1 and 2 |
| pseudouridine | 20 |
| dihydrouridine or 3-(3-amino-3-carboxypropyl)uridine | |
| N2-methylguanosine | 26 |
| N2, N2-dimethylguanosine | |
| 1-methylguanosine | 37 |
| unknown modified guanosine | |
| pseudouridine | 38 |
| pseudouridine | 39 |
| 2'-O-methyluridine | 44 |
| 5-methylcytidine | 48 |
| ribosylthymine | 52 |
| pseudouridine | 54 |

Having said that, any of the compounds in accordance with the first aspect may comprise one or more modifications as detailed further below, said modifications not being confined to non-natural modifications.

In a preferred embodiment of the derivative of the third aspect, said mutation is a substitution, deletion or insertion.

As noted above, any of the substitutions, deletions or insertions are preferably effected such that base pairing is maintained, to the extent said mutation affects a stem.

In a further preferred embodiment, said modification is selected from 2' modifications such as 2'-O-methyl, 2'-deoxy, 2'-fluoro; phosphate modifications such as thiophosphate; locked nucleic acids (LNA) and peptide nucleic acids (PNA). It is understood that the terms "LNA" and "PNA" include embodiments where a single modified nucleotide meets the requirement of LNA or PNA, respectively.

Further envisaged modifications of said compound and said derivative, respectively, include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Examples of compounds and derivatives include compounds and derivatives containing modified backbones or no natural internucleoside linkages. Compounds and derivatives having modified backbones include, among others, those that do not have a phosphorus atom in the backbone.

Modified backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Modified backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic inter-nucleoside linkages. These include those having morpholino linkages (formed in part from the sugar portion of a nucleo-side); siloxane backbones; sulfide, sulfoxide and sulfone backbones; formacetyl and thioformacetyl backbones; meth-ylene formacetyl and thioformacetyl backbones; alkene con-taining backbones; sulfamate backbones; methyleneimino and methylenehydrazino backbones; sulfonate and sulfona-mide backbones; amide backbones; and others having mixed N, O, S, and $CH_2$ component parts.

In other embodiments, compounds and derivatives are contemplated, in which both the sugar and the internucleo-side linkage, i.e., the backbone, of the nucleotide units are replaced with novel groups. The base units are maintained for hybridization with an appropriate nucleic acid target compound. One such compound or derivative that has been shown to have excellent hybridization properties, is referred to as a peptide nucleic acid (PNA). In PNA compounds, the sugar backbone of a polynucleotide is replaced with an amide containing backbone, in particular an aminoethylgly-cine backbone. The nucleobases are retained and are bound directly or indirectly to aza nitrogen atoms of the amide portion of the backbone.

Some embodiments featured in the invention include compounds and derivatives with phosphorothioate back-bones and oligonucleosides with heteroatom backbones, and in particular —$CH_2$—NH—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —N($CH_3$)—$CH_2$—$CH_2$— (wherein the native phosphodiester backbone is represented as —O—P—O—$CH_2$—).

Compounds and derivatives can also contain one or more substituted sugar moieties such as one of the following at the 2'-position: OH; F; O-, S-, or N-alkyl; O-, S-, or N-alkenyl; O-, S-, or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_n$ $OCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are indepen-dently 1, 2, 3, 4, 5, 6, 7, 8, 9 or 10. In other embodiments, compounds and derivatives include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalky-lamino, polyalkylamino, substituted silyl, an RNA cleaving group, a reporter group, an intercalator, a group for improv-ing the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxy-ethyl) or 2'-MOE) (Martin et al. (1995). *Helv. Chim. Acta*, 78:486-504) i.e., an alkoxy-alkoxy group. Another exem-plary modification is 2'-dimethylaminooxyethoxy, i.e., a $O(CH_2)_2ON(CH_3)_2$ group, also known as 2'-DMAOE, as described in examples herein below, and 2'-dimethylamino-ethoxyethoxy (also known in the art as 2'-O-dimethylami-noethoxyethyl or 2'-DMAEOE), i.e., 2'-O—$CH_2$—O—$CH_2$—N($CH_2$)_2.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other posi-tions, particularly the 3' position of the sugar on the 3' terminal nucleotide or in 2'-5' linked dsRNAs and the 5' position of 5' terminal nucleotide. Compounds and deriva-tives can also have sugar mimetics such as cyclobutyl moieties in place of the pentofuranosyl sugar.

Compounds and derivatives can also include nucleobase (often referred to in the art simply as "base") modifications or substitutions. As used herein, "unmodified" or "natural" nucleobases include the purine bases adenine (A) and gua-nine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-sub-stituted adenines and guanines, 5-halo, particularly 5-bromo, 5-trifluoromethyl and other 5-substituted uracils and cyto-sines, 7-methylguanine and 7-methyladenine, 8-azaguanine and 8-azaadenine, 7-deazaguanine and 7-daazaadenine and 3-deazaguanine and 3-deazaadenine. Modified nucleobases are present in glycol nucleic acids e.g., GNAs, e.g., thymi-dine-glycol nucleic acid, e.g., the S-isomer, cytidine-glycol nucleic acid, and adenosine-glycol nucleic acid (GNA) (see, e.g., US 20110306653). Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those dis-closed in The Concise Encyclopedia Of Polymer Science And Engineering, pages 858-859, Kroschwitz, J. L, ed. John Wiley & Sons, 1990; these disclosed by Englisch et al., Angewandte Chemie, International Edition, 1991, 30, 613; and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the bind-ing affinity of the oligomeric compounds featured in the invention. These include 5-substituted pyrimidines, 6-azapyrimidines and N-2, N-6, and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substi-tutions, even more particularly when combined with 2'-O-methoxyethyl sugar modifications.

Compounds and derivatives can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen et al. (2005). *Nucleic Acids Research* 33(1):439-447; Mook et al. (2007). *Mol Canc Ther* 6(3):833-843; Grunweller et al. (2003). *Nucleic Acids Research* 31(12):3185-3193).

Potentially stabilizing modifications to the ends of com-pounds and derivatives can include N-(acetylaminocaproyl)-4-hydroxyprolinol (Hyp-C6-NHAc), N-(caproyl-4-hy-droxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT).

In a fourth aspect, the present invention provides a tRNA$^{Leu(UAA)}$ derivative in accordance with the third aspect for use in medicine, preferably in a method of treating, ameliorating or preventing an infection with HIV virus, with SIV virus, with an Alphavirus and/or AIDS.

Accordingly, a separate aspect of the invention relates to a tRNA$^{Leu(UAA)}$ derivative in accordance with the third aspect for use in a method of treating, ameliorating or preventing an infection with HIV virus, with SIV virus, with an Alphavirus and/or AIDS.

In a fifth aspect, the present invention provides a pharmaceutical composition (a) comprising or (b) consisting of a compound as defined in accordance with the first or second aspect and/or a derivative as defined in accordance with the third aspect.

In a preferred embodiment, said pharmaceutical composition further comprises or further consists of one or more of the following: (i) a pharmaceutically acceptable carrier, excipient or diluent; and (ii) an anti-HIV agent, preferably an inhibitor of HIV reverse transcriptase, an inhibitor of HIV integrase, an inhibitor of HIV protease, a fusion inhibitor, i.e. a compound that blockes HIV entry into CD4 cells, a CCR5 antagonist, a post-attachment inhibitor, i.e. a compound that blocks HIV receptors on CD4 cells, a pharmacokinetic enhancer, an anti-miRNA agent, an siRNA or an shRNA, an RNA decoy, i.e. a compound that presents an exogenous RNA target for the HIV RNA-binding protein, a ribozyme, an mRNA-based drug, or a protein- or peptide-based anti-HIV agent.

As such, it is understood that said pharmaceutical composition may comprise a compound or a derivative in accordance with the present invention as the only pharmaceutically active agent. In the alternative, one or more such as two, three, four or five or more such as ten further pharmaceutically active agents may be present. In either case, non-active constituents such as the mentioned carrier, excipient or diluent may be present or absent.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration.

The compositions may also be administered directly to the target site, e.g., by biolistic delivery to an external or internal target site. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Pharmaceutically active matter in accordance with the invention may be present in amounts between 1 ng and 10 mg/kg body weight per dose; however, doses below or above this exemplary range are envisioned, especially considering the aforementioned factors. A dose is preferably a daily dose. If the regimen is a continuous infusion, it should be in the range of 1 μg to 10 mg units per kilogram of body weight per minute.

Particularly preferred are reverse transcriptase inhibitors and integrase inhibitors.

Preferred reverse transcriptase inhibitors are nucleoside analog reverse-transcriptase inhibitors (NARTIs or NRTIs); nucleotide analog reverse-transcriptase inhibitors (NtARTIs or NtRTIs); and non-nucleoside reverse-transcriptase inhibitors (NNRTIs). Specific reverse transcriptase inhibitors are zidovudine, didanosine, zalcitabine, stavudine, lamivudine, abacavir, emtricitabine, entecavir, tenofovir, and adefovir. Specific non-nucleoside reverse-transcriptase inhibitors (NNRTIs) are efavirenz, nevirapine, delavirdine, etravirine and rilpivirine.

Preferred integrase inhibitors include raltegravir, elvitegravir, dolutegravir and bictegravir.

Preferred protease inhibitors include amprenavir, atazanavir, darunavir, fosamprenavir, indinavir, nelfinavir, ritonavir, saquinavir, tipranavir.

Preferred fusion inhibitors include enfuvirtide.

Preferred CCR5 antagonists include maraviroc.

Preferred post-attachment inhibitors include ibalizumab.

Preferred pharmacokinetic enhancers include cobicistat.

Preferred agents for combination therapy also include the following ones (presently used for experimental treatment).

Preferred anti-miRNA and siRNA/shRNA therapeutics include Tat Rev shRNA (City of Hope, Benitec, in clinical trials).

Preferred decoys include TAR decoy (City of Hope, Benitec, in clinical trials) and RRE decoy (Children Hospital, Los Angeles, in clinical trials).

Preferred ribozymes include MY-2 (UCSD, completed), RRz1 (J&J, St. Vincent's Hospital, competed), OZ1 (Janssen-Cilag Pty Ltd, UCLA, in clinical trials), CCR5 (City of Hope, Benitec, in clinical trials) and L-TR/Tatneo (Ribozyme, City of Hope, completed).

Preferred mRNA-based drugs include CVS102, iHIVARNA-01 and AGS-004.

Preferred protein- and peptide-based drugs include dominant negative mutants HIV-1 Rev protein (Rev M10), dominant negative HIV-1 Rev protein, gp41 peptide, zinc finger nuclease targeting the CCR5 gene (SB-728) and CRISPR/Cas9 targeting the CCR5 gene.

In a sixth aspect, the present invention provides an in vitro or ex vivo method of reducing, abrogating or preventing HIV replication, virus particle formation and/or infectivity, said method comprising or consisting of administering a compound as defined in accordance with first or second aspect, a derivative as defined in accordance with the third aspect and/or a pharmaceutical composition of the fifth aspect, to a cell.

In an seventh aspect, the present invention provides an in vitro or ex vivo method of decreasing the ratio of Gag-Pol to Gag in HIV replication, said method comprising or consisting of administering a compound as defined in accordance with first or second aspect, a derivative as defined in accordance with the third aspect and/or a pharmaceutical composition of the fifth aspect, to a cell.

Amounts of Gag-Pol and of Gag and furthermore the ratio of the two may be determined by art-established methods. For example, infected cells may be lysed, proteins separated on a gel and identified by antibodies. Alternatively, virus particles per generation may be counted.

In relation to the sixth aspect, the present invention provides in an eighth aspect, the use of a compound as defined in accordance with first or second aspect, a derivative as defined in accordance with the third aspect, and/or a pharmaceutical composition of the fifth aspect, for reducing, abrogating or preventing HIV replication in a cell in vitro or ex vivo.

In relation to the seventh aspect, the present invention provides in a ninth aspect, the use of a compound as defined in accordance with first or second aspect, a derivative as defined in accordance with the third aspect, and/or a pharmaceutical composition of the fifth aspect, for decreasing the ratio of Gag-Pol to Gag in HIV replication in a cell in vitro or ex vivo.

In preferred embodiments of the methods and uses of the invention, said cell is a mammalian cell, a cell of a primate or a human cell.

In a tenth aspect, the present invention provides a kit comprising or consisting of a compound as defined in accordance with first or second aspect and/or a derivative as defined in accordance with the third aspect, said kit optionally comprising or further consisting of a manual with instruction for performing the method in accordance with sixth or seventh aspect of this invention.

As regards the embodiments characterized in this specification, in particular in the claims, it is intended that each embodiment mentioned in a dependent claim is combined with each embodiment of each claim (independent or dependent) said dependent claim depends from.

For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim, a first dependent claim referring back to, the independent claim, and a third dependent claim referring back to both the independent claim and the first dependent claim, it follows that the combination of the subject-matter of the second dependent claim and the independent claim is clearly and unambiguously disclosed as is the combination of the subject-matter of both the first and second dependent claims and the independent claim. In case a third dependent claim is present which refers to any one of the independent claim, or the first and second dependent claims, it follows that the combination of the subject-matter of the third dependent claim and the independent claim, of the third dependent claim, the first dependent claim, and the independent claim, of the third dependent claim, the second dependent claim, and the independent claim, as well as the combination of the first through third dependent claims and the independent claim is clearly and unambiguously disclosed.

The figures show:

FIG. 1: −1FS on HIV-1 gag-pol mRNA.

FIG. 1A. Scheme of the gag-pol frameshifting site. Slippery site (SS1, SEQ ID NO: 38) and the putative second slippery site (pSS2) are highlighted light grey; the stimulatory mRNA structure element downstream of the SS1 is indicated as a stem-loop (SL1). Amino acids incorporated into 0-frame and −1-frame peptides as well as the potential −1FS routes and in vivo efficiencies are shown below the frameshifting sites.

FIG. 1B. Top panel: Amino acids incorporated into 0- and −1-frames are shown above the mRNA sequence. Bottom panel: −1FS efficiency with the wild-type (wt) mRNA and $U_4C$ derivative with disrupted SS1 measured at limiting amounts of Leu-tRNA$^{Leu(UUA)}$ (molar ratio 0.3 tRNA to 70S ribosome). The 0-frame is the sum of MQANF (SEQ ID NO: 21) and MQANFLG (SEQ ID NO: 22) peptides, −1-frame corresponds to MQANFFR (SEQ ID NO: 23)/FLR peptides. MQANF (SEQ ID NO: 21) was identified based on its position on the chromatogram while MQANFFR (SEQ ID NO: 23)/FLR and MQANFLG (SEQ ID NO: 22) products were quantified using [$^{14}$C]Arg and [$^{3}$H]Gly, respectively. In the present drawing, the sequences shown are, respectively and from top to bottom, SEQ ID NOs:22-24 and SEQ ID NO: 39.

FIG. 1C. Concentration dependence of −1FS efficiency on the EF-Tu ternary complex (TC) with Leu-tRNA$^{Leu(UUA)}$ (Leu-UUA, closed circles) or with a mixture of tRNA$^{Leu}$ isoacceptors reading CUN codons (Leu-CUN, open circles) monitored at the end of translation (2 min). −1FS product was detected using [$^{14}$C]Arg.

FIG. 1D. Change in the FS regime with the Leu-tRNA$^{Leu}$ (UUA) concentration. The ratio of FFR route (open circles) vs. FLR (closed circles) route was calculated from peptides with different radioactive labels as follows. The sum of FFR and FLR frameshifting products was calculated using [$^{14}$C]Arg. To determine the amount of FLR, the mRNA was translated to the 0-frame peptide fMet-Gln-Asn-Phe-Leu-Gly-Lys-Ile (MQANFLGKI) (SEQ ID NO: 25). The presence of Ile allows for separation between 0-frame MQANFLGKI (SEQ ID NO: 25) and −1-frame MQANFLR (SEQ ID NO: 24) peptides. The FFR peptide was then determined by subtracting the FLR from the total Arg-containing product.

FIG. 1E. −1FS efficiency in the presence of varying concentrations of Gly-tRNA$^{Gly}$ in the presence of excess Arg-tRNA$^{Arg}$ (2 μM) (black circles) or with varying concentrations of Arg-tRNA$^{Arg}$ in the presence of 3 μM or 6 μM Gly-tRNA$^{Gly}$ (black and white squares, respectively).

FIG. 1F. (SEQ ID NOs: 32, 49, 50, 29, 40, 37 and 41) tRNA limitation results in −1, +1 and −2FS. Top panel shows the model mRNA and peptides synthesized in all frames. tRNAs for QANF (SEQ ID NO:37) were added to all translation reactions: other individual aa-tRNAs were supplied as indicated. Positions of peaks were determined using [$^{14}$C]-labeled Tyr, Met, Leu or Trp. In this drawing, the sequences shown are, respectively and from top to bottom, SEQ ID NOs: 32, 49, 50, 29, 40, 41, and 37.

FIG. 2: Kinetic mechanism of −1FS.

FIG. 2A. Time courses of translation in the absence of tRNA$^{Leu(UUA)}$. Peptides are MQAN (SEQ ID NO: 28). (circles), MQANF (SEQ ID NO: 21) (triangles), MQANFF (SEQ ID NO: 26) (crosses), and MQANFFR (SEQ ID NO: 23) (squares). Global fits are shown as continuous lines. The top panel shows amino acids in 0-frame and FFR −1-frame and respective codons on the mRNA. In this drawing, the sequences shown are, respectively and from top to bottom. SEQ ID NOs: 23, 21, 39, 28, 21, 26 and 23.

FIG. 2B. Kinetic model of the FFR pathway in the absence of tRNA$^{Leu(UUA)}$. Rates of all steps are calculated by global fitting In this drawing, the sequences shown are, from left to right are MOAN (SEQ ID NO: 28), MQANFFR (SEQ ID NO: 23), MQANFF (SEQ ID NO: 26), and MQANF (SEQ ID NO: 21).

FIG. 2C & FIG. 2D. Time courses of translation in the presence of limiting concentrations of tRNA$^{Leu(UUA)}$ (C, 0.3-fold per ribosome) and near-saturating concentrations of tRNA$^{Leu(UUA)}$ (D, 1-fold per ribosome). Peptides are MQAN (SEQ ID NO: 28) (circles), MQANF (SEQ ID NO: 21) (triangles), MQANFL (SEO ID NO: 27) (downward triangles), MQANFLG (SEQ ID NO: 22) (diamonds), and MQANFFR (SEQ ID NO: 23)/MQANFLR (SEQ ID NO: 24) (squares). Global fits are shown as continuous lines. The top panel shows amino acids in 0-frame and −1-frame and respective codons on the mRNA. In FIG. 2C, the sequences shown are, respectively and from top to bottom, SEQ ID NOs: 24, 23, 22, 39, 28, 21, 27, 22, and 23. In FIG. 2D, the sequences shown are, respectively and from top to bottom, SEQ ID NOs: 28, 21, 27, 22, and 23.

FIG. 2E. Kinetic model of the FFR/FFL pathways. Rates of all steps are calculated by global fitting. 0- and −1-frames are indicated by dotted arrows. *Incorporation of Leu-tRNA$^{Leu(UUA)}$ is a bimolecular reaction and its rate depends on the concentration of tRNA$^{Leu(UUA)}$. The two rates correspond to 0.3- and 1.0-fold excess of tRNA$^{Leu(UUA)}$ over ribosomes, respectively. In this drawing, the sequences shown are MOAN (SEQ ID NO: 28), MQANF (SEQ ID NO:21), MQANFF (SEQ ID NO:26) MQANFFR (SEQ ID NO:23), MQANFL (SEQ ID NO:27), MQANFLR (SEQ ID NO:24), and MQANFLG (SEQ ID NO:22).

FIG. 3: Translation and frameshifting with the native human aa-tRNA.

Figures 3A, 3B, 3C, 3D, 3E:
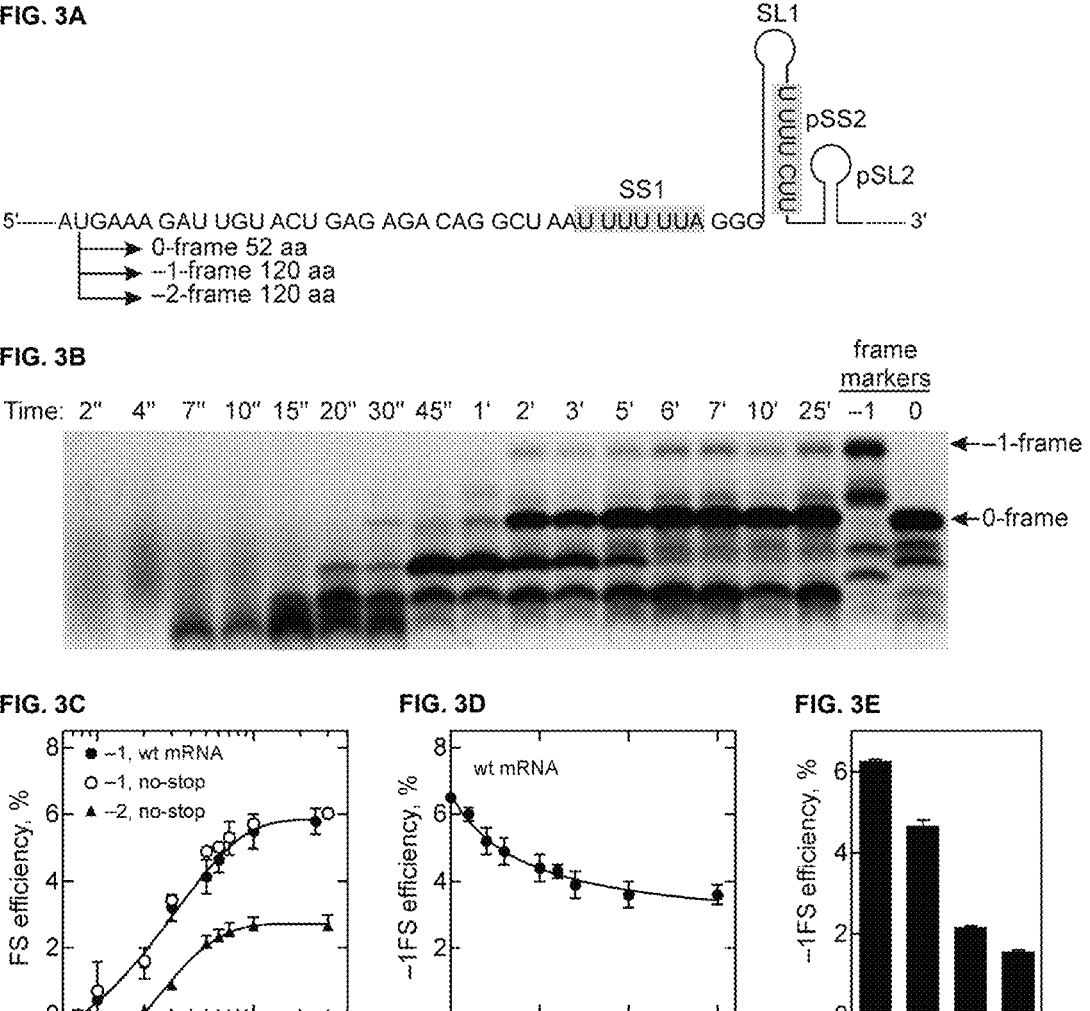

FIG. 3A. The mRNA used for translation experiments. SS1 and pSS2 are highlighted light grey, SL1 and the potential stem-loop element downstream of the pSS2 (pSL2) are shown. Sizes of 0-, −1- and −2-frame peptides formed upon translation of the mRNA are indicated. In this figure, the sequence shown is SEQ ID NO: 42.

FIG. 3B. Time course of 0-frame and −1-frame translation on wt mRNA.

FIG. 3C. Time courses of −1FS on wt mRNA (closed circles) as well as −1FS (open circles) and −2FS (closed triangles) on mRNA where all stop codons in −2-frame were mutated to sense codons (no-stop).

FIG. 3D) Concentration dependence of −1FS efficiency on exogenous tRNA$^{Leu(UUA)}$ from E. coli measured on wt mRNA.

FIG. 3E) Effect of mutations in SS1 on −1FS. The background of the measurements is 1%. The s.e.m was calculated from 3-5 independent experiments.

FIG. 4: Schematic drawing of a preferred compound in accordance with the present invention.

The nomenclature used for loops and stems is that generally used for tRNAs. A base designated as "N" may be any base selected from A, C, G and U, provided that the N facing said base on the opposite strand within the same stem is capable of base pairing. For example, an A on one strand implies a U on the other strand as a specific implementation of a base pair N—N. The sequence depicted in FIG. 4 is that of SEQ ID NO: 1.

Figure 5:
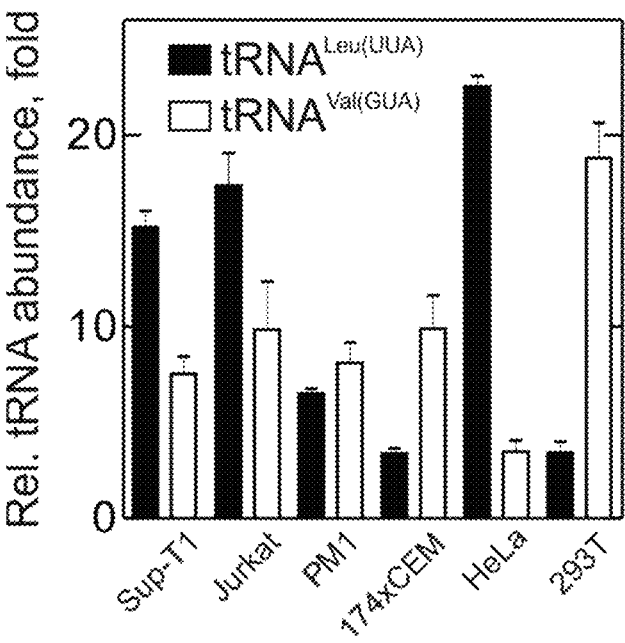

FIG. 5. tRNA$^{Leu(UUA)}$ is rare in different human cell types. Plotted is the ratio of tRNA$^{Leu(UUA)}$ (major isoacceptor) to tRNA$^{Leu(UUA)}$ (black bars) and tRNA$^{Val(GUG)}$ to tRNA$^{Val(GUA)}$ (white bars), that read frequent and rare codons, respectively, in human cell lines. Error bars represent s.e.m of three biological replicates with three technical replicates each. Human cell lines are indicated below the graph. Sup-T1, Jurkat and PMI are derived from human T-lymphocytes: 174×CEM is B-T-lymphocyte fusion: HeLa are derived from cervical epithelial carcinoma; 293T is a kidney epithelial cell line.

FIG. 6. Translation of the eukaryotic gag-pol wt mRNA using a fully reconstituted homologous mammalian in vitro translation system.

Figure 6A:
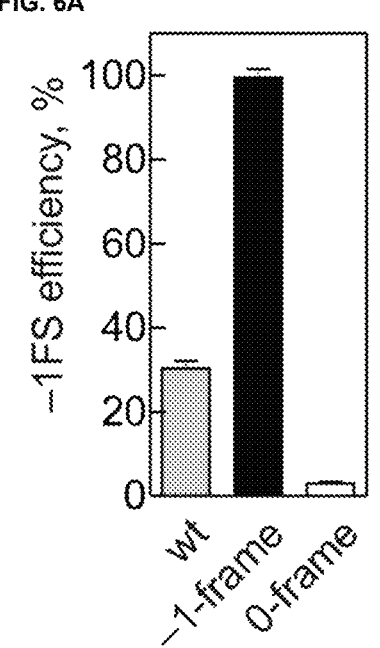

FIG. 6A −1FS efficiency measured with wt (grey bar), −1-frame control (black bar) and 0-frame control (white bar) HIV mRNAs.

Figure 6B:
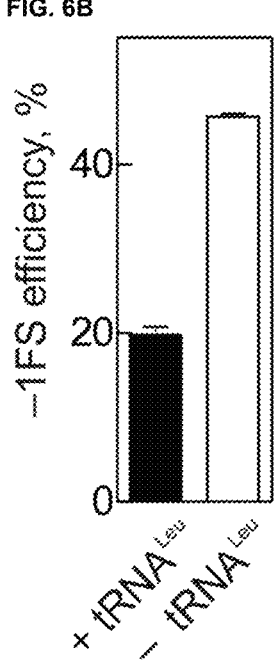

FIG. 6B −1FS efficiency measured with wt HIV-1 mRNA in the presence (+tRNA$^{Leu}$) and in the absence (−tRNA$^{Leu}$) of total Leu-tRNA$^{Leu}$ containing all isoacceptors in native ratios. The −1-frame peptide was identified based on [$^3$H] Arg incorporation.

FIG. 7. Mechanism of −1FS on the alphavirus SFV 6K mRNA.

Figure 7A:
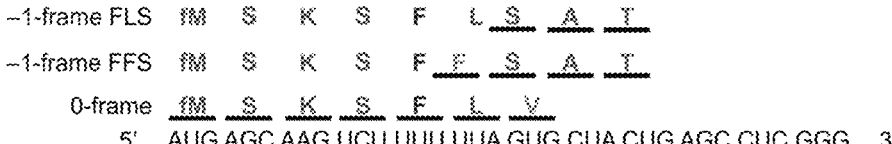

FIG. 7A Schematic of the frameshifting site. The model SFV mRNA containing native SS and SL is optimized for translation in E. coli by introducing a SD sequence and a start codon AUG followed by AAG (Lys) to improve translation efficiency. The sequences shown in this drawing are, respectively and from top to bottom, SEQ ID NOs: 43, 44, 45, and 45.

Figure 7B:
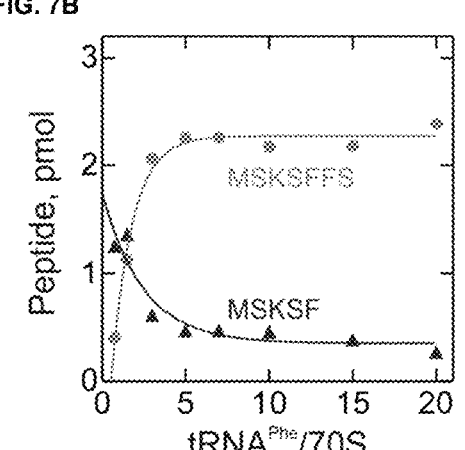

FIG. 7B Effect of Phe-tRNA$^{Phe}$ on FFS peptide formation in the absence of Leu-tRNA$^{Leu(UUA)}$. Translation was carried out using tRNAs aminoacylated with M, S, K, F. The sequences shown in this drawing are, respectively and from top to bottom, SEQ ID NOs: 47 and 48.

Figure 7C:
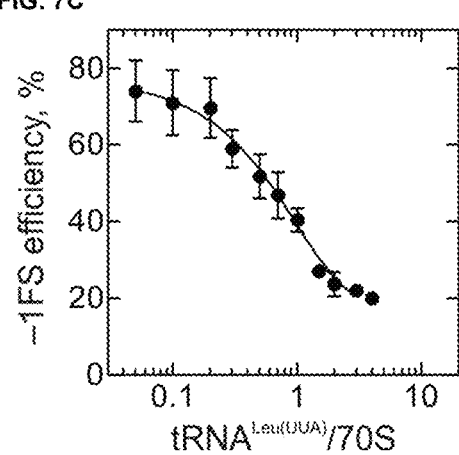

FIG. 7C Dependence of −1FS on Leu-tRNA$^{Leu(UUA)}$ concentration. Translation was carried out with M, S, K, F, L, V, A and T aa-tRNAs.

The examples illustrate the invention.

Example 1

Materials and Methods
Materials

Chemicals were purchased from Sigma, Roche or Merck, radioactive-labeled amino acids were from Hartman Analytic. 70S ribosomes from MRE600, initiation factors (IF1, IF2, IF3), elongation factors (EF-Tu, EF-G), RF1, fMet-tRNA$^{fMet}$, BODIPY-Met-tRNA$^{fMet}$ and Phe-tRNA$^{Phe}$ were prepared from E. coli as described (Cunha et al. (2013). Translation 1, e24315; Doerfel et al. (2013). Science 339, 85-88; Florin et al. (2017). Nat Struct Mol Biol 24, 752-757; Milon et al. (2007). Methods Enzymol 430, 1-30; Mittelstaet et al. (2013). J Am Chem Soc 135, 17031-17038; Rodnina et al. (1999). Proceedings of the National Academy of Sciences of the United States of America 96, 9586-9590; Savelsbergh et al. (2003). Mol Cell 11, 1517-1523). Gln-, Ala-, and Asn-tRNA mixture, Arg-tRNA$^{Arg}$, Gly-tRNA$^{Gly}$, Val-tRNA$^{Val}$ were prepared from E. coli total tRNA by aminoacylation with the respective amino acid and subsequent affinity chromatography of the EF-Tu-GTP-aa-tRNA ternary complexes on Protino Ni-IDA 2000 Packed Columns (Macherey-Nagel) followed by phenolization and ethanol precipitation of aa-tRNA. tRNA$^{Leu(UUA)}$, elongator tRNA$^{Met}$, tRNA$^{Tyr}$, and a mixture of isoacceptors tRNA$^{Leu(CUN)}$ were prepared by consecutive column chromatographies on Sepharose 4B (GE Healthcare), Phenyl Sepharose (GE Healthcare), and DEAE Toyopearl (Tosoh Bioscience). tRNA$^{Trp}$ was prepared by T7 RNA-polymerase transcription from pUC18 plasmid carrying the E. coli trp gene (Korencic et al. (2002). Nucleic Acids Res 30, e105). tRNAs were charged with $^{14}$C-, or $^3$H-labeled or unlabeled amino acids (Kothe et al. (2006). Anal Biochem 356, 148-150). Leu-tRNA$^{Leu(UUA)}$, mixture of isoacceptors Leu-tRNA$^{Leu(CUN)}$, Met-tRNA$_e^{Met}$, and Tyr-tRNA$^{Tyr}$ were purified by reversed-phase HPLC on a WP-300 RP-18 column (250 mm×10.5 mm, Merck) equilibrated with 20 mM ammonium acetate, pH 5.0, 10 mM magnesium acetate, 400 mM NaCl using a gradient of 0%-15% ethanol. Concentrations were determined spectrophotometrically at 260 nm and by liquid-liquid scintillation counting where applicable (Ultima Gold, Perkin Elmer). Total human aa-tRNA was prepared from HeLa cell extracts. The cytoplasmic fraction of the cell lysate was phenolized and aa-tRNA was purified by cation-exchange chromatography on a HiTrap Q HP column (5 mL, GE Healthcare) equilibrated with 50 mM sodium acetate, pH 4.5 and 10 mM $MgCl_2$ using a gradient of 0-1.1 M KCl.

We used a native sequence of the gag-pol HIV-1 frame-shifting motif (nt 1601-1961 in the HIV-1 complete genome, NCBI Reference Sequence NC_001802.1) cloned into pEX-A2 vector. Mutations were introduced by site-directed muta-genesis using Q5 DNA-polymerase (NEB) (Mullis (1990). Ann Biol Clin (Paris) 48, 579-582). mRNAs were prepared by in vitro transcription with T7 RNA-polymerase (Milligan et al. (1987). Nucleic Acids Res 15, 8783-8798; Tabor and Richardson (1985). Proc Natl Acad Sci USA 82, 1074-1078) and purified by RNeasy maxi kit (Qiagen) according to the manufacture's recommendations. Control mRNAs used to determine the rate of Arg-tRNA[Arg] incorporation in 0-frame were made by chemical synthesis (IBA, Gottingen) and contained an *E. coli* Shine-Dalgarno (SD) sequence inserted 9 nt upstream of the start codon AUG. In HIV mRNAs a SD sequence was inserted 6 nt upstream of the start codon AUG. In the short mRNAs used in the codon walk experiments, AUG was introduced 8 nt upstream of the slippery site. In the mRNAs used to study +1 and −2 frameshifting, the GGG codon (Gly) following the slippery site was mutated to UGG (Trp) to distinguish between the −1-, −2- and +1-frameshift-ing products (Mathew et al. (2015). PLoS One 10, e0122176). The nearest natural AUG in gag mRNA was used as a start codon in the long mRNAs to study gag-pol translation products by PAGE. The stop codon UAG was introduced in the 0-frame 156 nt downstream of the AUG and 120 nt after the SS1 to allow the separation between the 0-frame (52 aa) and −1-frame (120 aa) products. 0-, −1- and −2-frame control mRNAs contain respective sequence cloned in-frame with SS1 and pSS2 being mutated to prevent slippages.

The following mRNAs were used (AUG is in bold, slippery sites are underlined, UAG stop codon in 0-frame is in italic, and mutated nucleotides are in small letters in bold):

```
Short mRNAs for codon-walk experiments:
wt short mRNA HPLC:
                             (SEQ ID NO: 12)
GGGAGACCGGAAUUCGAGCUCGCCCAAACGCGGUUGGAUUCCUGAUGAA

AAGUUCUAUGAGGGUGUAUAAUGCAGGCUAAUUUUUUUAGGGAAGAUCUGG

CCUUCCUACAAGGGAAGGCCAGGGAAUUUUCUUCAGAGCAGACC

U4C mRNA HPLC:
                             (SEQ ID NO: 13)
GGGAGACCGGAAUUCGAGCUCGCCCAAACGCGGUUGGAUUCCUGAUGAA

AAGUUCUAUGAGGGUGUAUAAUGCAGGCUAAUUUUcUUAGGGAAGAUCUGG

CCUUCCUACAAGGGAAGGCCAGGGAAUUUUCUUCAGAGCAGACC

-2/+1 mRNA HPLC:
                             (SEQ ID NO: 14)
GGGAGACCGGAAUUCGAGCUCGCCCAAACGCGGUUGGAUUCCUGAUGAA

AAGUUCUAUGAGGGUGUAUAAUGCAGGCUAAUUUUUUAuGGAAGAUCUGG

CCUUCCUACAAGGGAAGGCCAGGGAAUUUUCUUCAGAGCAGACC
```

-continued

```
Long mRNAs for translation:
wt long mRNA gel:
                             (SEQ ID NO: 15)
GGGAGACCGGAAUUCGAGCUCGCCCAAACGCGGUUGGAUUCCUGAUGAA

AAGUUCUAUGAGGGUGUAUAAUGAAAGAUUGUACUGAGAGACAGGCUAAU

UUUUUAGGGAAGAUCUGGCCUUCCUACAAGGGAAGGCCAGGGAAUUUUC

UUCAGAGCAGACCAGAGCCAACAGCCCCACCAGAAGAGAGCUUCAGGUC

UGGGGUAGAGACAACAACUCCCCCUCAGUAGCAGGAGCCGAUAGACAAG

GAACUGUAUCCUUUAACUUCCCUCAGGUCACUCUUUGGCAACGACCCCU

CGUCACAAUAAAGAUAGGGGGGCAACUAAAGGAAGCUCUAUUAGAUACA

GGAGCAGAUGAUACAGUAUUAGAAGAAAUGAGUUUGCCAGGAAGAUGGA

AACCAAAAAUGAUAGGGGGAAUUGGAGGUUUUAUCA 0-frame control mRNA gel:
                             (SEQ ID NO: 16)
GGGAGACCGGAAUUCGAGCUCGCCCAAACGCGGUUGGAUUCCUGAUGAA AAGUUCUAUGAGGGUGUAUAAUGAAAGAUUGUACUGAGAGACAGGCUAAc UUcgUAGGGAAGAUCUGGCCUUCCUACAAGGGAAGGCCAGGGAAUUUcC

UUCAGAGCAGACCAGAGCCAACAGCCCCACCAGAAGAGAGCUUCAGGUC

UGGGGUAGAGACAACAACUCCCCCUCAGUAGCAGGAGCCGAUAGACAAG

GAACUGUAUCCUUUAACUUCCCUCAGGUCACUCUUUGGCAACGACCCCU

CGUCACAAUAAAGAUAGGGGGGCAACUAAAGGAAGCUCUAUUAGAUACA

GGAGCAGAUGAUACAGUAUUAGAAGAAAUGAGUUUGCCAGGAAGAUGGA

AACCAAAAAUGAUAGGGGGAAUUGGAGGUUUUAUCA

-1-frame control mRNA gel:
                             (SEQ ID NO: 17)
GGGAGACCGGAAUUCGAGCUCGCCCAAACGCGGUUGGAUUCCUGAUGAA AAGUUCUAUGAGGGUGUAUAAUGAAAGAUUGUACUGAGAGACAGGCUAAc UUcgUAaGGGAAGAUCUGGCCUUCCUACAAGGGAAGGCCAGGGAAUUUc

CUUCAGAGCAGACCAGAGCCAACAGCCCCACCAGAAGAGAGCUUCAGGU

CUGGGGUAGAGACAACAACUCCCCCUCAGUAGCAGGAGCCGAUAGACAA

GGAACUGUAUCCUUUAACUUCCCUCAGGUCACUCUUUGGCAACGACCCC

UCGUCACAAUAAAGAUAGGGGGGCAACUAAAGGAAGCUCUAUUAGAUAC

AGGAGCAGAUGAUACAGUAUUAGAAGAAAUGAGUUUGCCAGGAAGAUGG

AAACCAAAAAUGAUAGGGGGAAUUGGAGGUUUUAUCA

-2-frame control mRNA gel:
                             (SEQ ID NO: 18)
GGGAGACCGGAAUUCGAGCUCGCCCAAACGCGGUUGGAUUCCUGAUGAA AAGUUCUAUGAGGGUGUAUAAUGAAAGAUUGUACUGAGAGACAGGCUAAc UUcgUAaGGGAAGAUCUGGCCUUCCUACAAGGGAAGGCCAGGGAAUUUc CUUuCAGAGCAGACCAGAGCCAACAGCCCCACCAGAAGAGAGCUUCAGG UCUGGGGUcGAGACAACAACUCCCCCUCAGUAGCAGGAGCCGAUcGACA AGGAACUGUAUCCUUUcACUUCCCUCAGGUCACUCUUUGGCAACGACCC

CUCGUCACAAUAAAGAUAGGGGGGCAACUAAAGGAAGCUCUAUUAGAUA

CAGGAGCAGAUCAUACAGUAUUAGAAGAAAUGAGUUUGCCAGGAAGAUG

GAAACCAAAAAUGAUAGGGGGAAUUGGAGGUUUUAUCA
```

Mutant mRNA constructs had the same sequence as the wild-type mRNA, except for mutations in the slippery sites SS1 and pSS2 or pSL2.

Control mRNAs used to determine the rate of Arg-tRNA$^{Arg}$ incorporation in 0-frame

```
fM-F-R(AGG)-Stop
                                    (SEQ ID NO: 19)
GUUAACAGGUAUACAUACUAUGUUCAGGAUUAC fM-L-R(AGG)-Stop
                                    (SEQ ID NO: 20)
GUUAACAGGUAUACAUACUAUGUUAAGGAUUAC
```

Buffer

All experiments were carried out in HiFi buffer (50 mM Tris-HCl, pH 7.5, 70 mM NH$_4$Cl, 30 mM KCl, 3.5 mM MgCl$_2$, 8 mM putrescine, 0.5 mM spermidine, 1 mM DTT) at 37° C. if not stated otherwise.

Preparation of Initiation Complexes (IC)

ICs were prepared by incubating 70S ribosomes (1 μM) with mRNA (3-10 μM), initiation factors IF1, IF2, and IF3 (1.5 μM each), initiator f[$^3$H]Met-tRNA$^{fMet}$ or BODIPY-Met-tRNA$^{fMet}$ (2 μM), DTT (1 mM) and GTP (1 mM) in buffer A (50 mM Tris-HCl, pH 7.5, 70 mM NH$_4$Cl, 30 mM KCl, 7 mM MgCl$_2$) for 30 min at 37° C. ICs used in the codon walk experiments were purified by ultracentrifugation through a 1.1 M sucrose cushion in buffer A and dissolved in HiFi buffer.

Codon Walk Assay

To form EF-Tu-GTP-aa-tRNA ternary complexes (TCs), EF-Tu (25-30 μM, or 3-fold excess over aa-tRNA) was incubated with GTP (1 mM), phosphoenolpyruvate (3 mM), and pyruvate kinase (0.1 mg/ml) in buffer A with DTT (1 mM) for 15 min at 37° C. Then, aa-tRNAs were added and incubated for 1 min at 37° C. The concentrations of aa-tRNA were optimized to ensure the maximum binding at each codon, 1.6 μM for Gln-tRNA$^{Gln}$, Ala-tRNA$^{Ala}$, Asn-tRNA$^{Asn}$, Phe-tRNA$^{Phe}$, and Arg-tRNA$^{Arg}$ each, 1.2 μM for Gly-tRNA$^{Gly}$, and different concentrations of Leu-tRNA$^{Leu(UUA)}$ as indicated. IC (0.16 μM) was mixed with TCs (about 20 μM final concentration of EF-Tu), EF-G (1.6 μM), GTP (1 mM) phosphoenolpyruvate (2.4 mM), and pyruvate kinase (0.08 mg/ml) in HiFi buffer at 37° C. Incubation times were 0-10 min for time courses or 2 min for single-time measurements. The stability of peptidyl-tRNA binding to the ribosome was tested by nitrocellulose filter binding assay. To prepare samples for the HPLC analysis, the reactions were quenched with KOH (0.5 M) and hydrolyzed for 30 min at 37° C. and the pH neutralized by the addition of acetic acid. Translation products were then separated by the reversed-phase HPLC using RP-8 column (LiChroSpher100, Merck) using an adapted gradient of acetonitrile (0-65%) with 0.1% TFA. Eluted fractions were mixed with Ultima Gold scintillation liquid (Perkin Elmer) and analyzed by scintillation counting. The peptide products up to MQAN (SEQ ID NO: 28) were not separated from each other, but all other peptides can be identified by either position shift on a chromatogram or incorporation of the radioactive label of the respective amino acid. The amount of each product was determined as a ratio between [$^3$H]-counts in the respective peak and total [$^3$H]-counts in the eluate. For samples with [$^3$H]Gly-tRNA$^{Gly}$ and [$^{14}$C]Arg-tRNA$^{Arg}$ or [$^{14}$C]Leu-tRNA$^{Leu(UUA)}$ respective peaks were calculated in pmol. Where necessary, the amount of MQAN-FLR (SEQ ID NO; 24) peptide was calculated by subtracting MQANFLG (SEQ ID NO: 22) from MQANFL (SEQ ID NO: 27), in pmol. Likewise, MQANFFR (SEQ ID NO: 23) peptide was calculated by subtracting MQANFLR (SEQ ID NO: 24) from the MQANFLR (SEQ ID NO: 24)/FFR mixture product, in pmol. Time courses were evaluated by numerical integration in KinTek software (Johnson (2009). Fitting enzyme kinetic data with KinTek Global Kinetic Explorer. Methods in enzymology 467, 601-626). Frameshifting efficiency was calculated as a ratio between the −1-frame peptide (MQANFFR (SEQ ID NO: 23) and MQANFLR (SEQ ID NO: 24) and the sum of −1- and all 0-frame peptides (MQANF (SEQ ID NO: 21), MQANFL (SEQ ID NO: 27). MQANFLG (SEQ ID NO: 22)), multiplied by 100%.

Quantification of tRNA levels using qRT-PCR and translation of HIV mRNAs in a fully reconstituted homologous mammalian in vitro translation system were carried out as described (Komiy, N., Goyal, A., Hoffmann, M., Samatova, E., Peske. F., Pöhlmann, S. and Rodnina, M. V. (2019). Modulation of HIV-1 Gag/Gag-Pol Frameshifting by tRNA abundance. Nucleic Acids Res 47(10):5210-5222).

End-Point Translation Assay of −2: +1 mRNA

Translation of −2/+1 was carried out as described for the codon walk assay, but with 0.4 μM of Gln-tRNA$^{Gln}$, Ala-tRNA$^{Ala}$, Asn-tRNA$^{Asn}$ each, 0.8 μM of Phe-tRNA$^{Phe}$ and Leu-tRNA$^{Leu(UUA)}$, and 0.4 μM of Trp-tRNA$^{Trp}$, Met-tRNA$_e^{Met}$, and Tyr-tRNA$^{Tyr}$ each. IC (0.08 μM) was mixed with TCs (about 10 μM final concentration of EF-Tu), EF-G (1.6 μM), GTP (1 mM) phosphoenolpyruvate (2.4 mM), and pyruvate kinase (0.08 mg/ml) in HiFi buffer at 37° C. The efficiency of frameshifting peptide synthesis was calculated by dividing the amount of the respective peptide in pmol by the sum of all peptides in translation excluding MQAN (SEQ ID NO: 28), multiplied by 100%.

Arg-tRNA$^{Arg}$ Incorporation Assay

To form post-translocation complexes, purified ICs (0.16 μM final) were mixed with Phe-tRNA$^{Phe}$ (1.6 μM) or Leu-tRNA$^{Leu(UUA)}$ (0.16 μM) in the presence of EF-G (0.008 μM, ⅟20 of the IC concentration) in HiFi buffer and incubated for 1 min at 37° C. Post-translocation complexes were then mixed with Arg-tRNA$^{Arg}$ (1.6 μM) and EF-G (1.6 μM) and reacted for 1-100 s at 37° C. The position of MFR and MLR peptides was identified based on [$^{14}$C]Arg counts and their amounts were calculated in pmol. The rate of Arg incorporation was estimated by exponential fitting in GraphPad Prism software.

Translation Assay

IC prepared with BODIPY-Met-tRNA$^{fMet}$ (0.08 μM) was incubated with EF-Tu (80 μM), total aa-tRNA from HeLa (3-10 μM), EF-G (1.6 μM) and RF1 (0.8 μM), GTP (1 mM), phosphoenolpyruvate (2.4 mM), and pyruvate kinase (0.08 mg/ml) in HiFi buffer at 37° C. as indicated in the time course of translation or for 30 min for single-point measurements. In case of γB-crystallin, translation was carried out using IC (0.02 μM), EF-Tu (45 μM), total aa-tRNA from HeLa (10 μM), EF-G (1 μM), GTP (0.8 mM), phosphoenolpyruvate (1.4 mM), and pyruvate kinase (0.05 mg/ml) for 30 min in HiFi buffer at 37° C. To prepare the samples for PAGE, the reactions were stopped by NaOH (0.4 M) and hydrolyzed as described for the HPLC sample preparation. HEPES (0.2 M, pH 5) was added to neutralize the reactions. The samples were separated by Tris-Tricine gel electrophoresis (Schagger and von Jagow (1987). Anal Biochem 166, 368-379). Fluorescent peptides were visualized using an FLA-9000 scanner (Fuji Photo Film Co., Ltd) and the band intensities were evaluated using the MultiGauge software. Frameshifting efficiency was calculated from the band intensities of the −1-frame product to the sum of −1- and 0-frames products as well as of translation intermediates appearing at 20 s of translation. The correct length of the peptides was confirmed using control 0-frame, −1-frame and −2-frame mRNAs.

Translation of the alphavirus SFV 6K mRNA was performed as described (Korniy, N. Sarnatova, E., Anokhina, M. M., Peske, F. and Rodnina, M. V. (2019). Mechanisms and biomedical implications of −1 programmed ribosome frameshifting on viral and bacterial mRNAs. FEBS Lett. doi: 10.1002/1873-3468.13478. [Epub ahead of print]).

Example 2

Results
Two Regimes for −1FS on the Gag-Pol Slippery Site

We first tested the potential routes for frameshifting using a fully reconstituted *E. coli* translation system. The model HIV-1 gag-pol mRNA encompasses the natural frameshifting site with the translation start codon AUG three codons upstream of the slippery site (FIG. 1B). We formed a 70S initiation complex with the mRNA and fMet-tRNA$^{fMet}$ and started translation by the addition of ternary complexes EF-Tu-GTP with the desired combination of purified aa-tRNAs and EF-G-GTP. Consecutive amino acids incorporation results in a 0-frame peptide fMet-Gln-Ala-Asn-Phe-Leu-Gly (MQANFLG (SEQ ID NO: 22)) and the −1-frame peptides fMet-Gln-Ala-Asn-Phe-Leu-Arg (MQANFLR (SEQ ID NO: 24)) or fMet-Gln-Ala-Asn-Phe-Phe-Arg (MQANFFR (SEQ ID NO: 23)). Peptides were analyzed by reverse-phase HPLC (RP-HPLC). The overall frameshifting efficiency was determined as a ratio of −1-frame Arg incorporation to the sum of −1- and 0-frame peptides. With the mRNA containing a native slippery sequence, a large fraction of peptides contains Arg (FIG. 1B), suggesting efficient −1FS. As expected, U$_4$C mutation in the SS abolishes FS.

We then identified the mechanism of −1FS on SS1. We used our experimental toolbox developed for probing the mechanisms of −1FS (Caliskan et al., 2014; Caliskan et al., 2017). In principle, −1FS can occur during decoding when only peptidyl-tRNA is bound in the P site of the ribosome while the A-site is vacant (Caliskan et al. (2017). Mol Cell 66, 558-567 e554; Yelverton et al. (1994). Mol Microbiol 11, 303-313). If slippage occurred during decoding, the frameshifting efficiency must depend on the competition between the 0-frame and −1-frame aa-tRNAs, i.e. between Leu-tRNA and Phe-tRNA for the UUA codon of the slippery sequence. In fact, addition of Leu-tRNA$^{Leu(UUA)}$ has a dramatic effect on −1FS, changing the frameshifting efficiency from about 50% in the absence to about 15% in the presence of Leu-tRNA$^{Leu(UUA)}$ (FIG. 1C). In contrast, a mixture of near-cognate Leu-tRNA isoacceptors that collectively read the CUN family of Leu codons has no effect. The high −1FS efficiency observed in the absence of Leu-tRNA$^{Leu(UUA)}$ indicates that ribosomes can slip into −1-frame prior to and independent of Leu incorporation. In human cells the Leu codon UUA is rare (8% of Leu codons), but it is abundant in the late HIV genes including gag and pol. UUA is decoded by Leu-tRNA$^{Leu(UUA)}$, which has a very low abundance in eukaryotic cells (Dittmar et al. (2006). PLoS Genet 2, e221; Sharp et al. (1988). Nucleic Acids Res 16, 8207-8211; van Weringh et al. (2011). Mol Biol Evol 28, 1827-1834).

By estimating the ratio of Leu, Phe and Arg incorporation into the −1-frame product, we could determine how the pathway changes with Leu-tRNA$^{Leu(UUA)}$ concentration (FIG. 1D). In the absence of Leu-tRNA$^{Leu(UUA)}$, only the FFR −1-frame product is formed. Upon addition of Leu, the amount of the FFR product decreases, whereas the FLR product becomes prevalent at high Leu-tRNA$^{Leu(UUA)}$ concentrations. Thus, frameshifting at the gag-pol slippery site can switch between two regimes and their relative abundance depends on the concentration of the particular tRNA.

After Leu incorporation, −1FS can potentially follow different routes: it can occur during tRNA$^{Leu}$ translocation or upon decoding of the following Gly codon. Again, if frameshifting takes place during decoding, the 0-frame Gly-tRNA$^{Gly}$ and −1-frame Arg-tRNA$^{Arg}$ should compete for binding. This is, however, not observed, as −1FS efficiency is independent of Gly-tRNA$^{Gly}$ and is hardly affected by increasing Arg-tRNA$^{Arg}$ concentrations (FIG. 1E); a small increase in Arg incorporation is independent of the tRNA$^{Gly}$ concentration and thus does not result from a competition between those two aa-tRNAs. This finding suggests that the slippage and the commitment to the new reading frame occur after Leu incorporation, but prior to reading of the next codon by Gly- or Arg-tRNAs.

Because formation of the −1-frame FFR product appears to constitutively depend on the slippage at the "hungry" UUA codon, we further tested whether this allows also −2 and +1FS. We note that normally such slippage events would lead to premature termination due to stop codons appearing in the −2 or +1 frames downstream of the frameshifting site and that such peptides are difficult to detect in vivo, but alternative slippage events could change the ratio between the Gag and Gag-Pol polyproteins. To distinguish between the products of the 0-, −1-, −2- and +1-frames, we mutated the GGG (Gly) codon following the slippery site into UGG (Trp) (FIG. 1F); the mutation does not affect the −1FS efficiency in vivo in human cells (Mathew et al. (2015). PLoS One 10, e0122176). In addition to the tRNAs needed for translation of the MQANFL (SEQ ID NO: 27) sequence, we add purified Trp-tRNA$^{Trp}$ (W), elongator Met-tRNA$^{Met}$ (M) and Tyr-tRNA$^{Tyr}$ (Y). The expected 0-frame peptide is MQANFLW (SEQ ID NO: 29), whereas the −1-frame peptides are now MQANFFM (SEQ ID NO: 30) and MQANFLM (SEQ ID NO: 31). Shifting into the +1-frame should yield MQANFY (SEQ ID NO: 32) and into the −2-frame MQANFFY (SEQ ID NO: 35) and MQANFLY (SEQ ID NO: 36). When all aa-tRNAs are present, the −1-frame peptides account for 20% of product, consistent with the −1FS efficiency on the native gag-pol sequence in the presence of Leu-tRNA$^{Leu(UUA)}$ (FIG. 1F), whereas the amounts of the +1 and −2 peptides are negligible. In the absence of Leu- and Trp-tRNAs, the efficiency of −1FS increases to >45%, as expected: −2FS is unchanged; and a small, but significant amounts of the +1-frame product is formed. −2FS is unchanged; and a small, but significant amount of the +1-frame product is formed. −2FS and +1FS can occur because −1FS exposes a "hungry" Met codon in the A site, favoring further slippage. Without Leu-, Trp-, and Met-tRNA, the products of all three frames are found. These data suggest that −2 and +1FS can occur when one or more aa-tRNAs are lacking, however at conditions where all aa-tRNAs are available only the −1FS pathway is operational.

Kinetics of FFR and FLR Routes

To understand the two different FS regimes, we monitored translation and frameshifting using the codon-walk approach (Caliskan et al. (2014). Cell 157, 1619-1631) in the absence and presence of Leu-tRNA$^{Leu(UUA)}$ (FIG. 2). Rate constants were calculated by global fitting of the time courses by numerical integration according to the models shown in FIG. 2. As additional information, we estimated the rate constants of Arg and Gly incorporation in independent experiments using model mRNAs without frameshifting elements.

For the −1FS model in the absence of Leu-tRNA$^{Leu(UUA)}$, we introduced the steps that result in the formation of MQANF (SEQ ID NO: 21) and the −1FS products MQANFF (SEQ ID NO: 26) and MQANFFR (SEQ ID NO: 23). In addition, we introduced two reaction branches that account for the incomplete conversion of the 70S IC into products as follows. Because a fraction of initiation complexes does not enter translation, we introduce a step that accounts for the existence of this unproductive population (M→Mn, non-reactive). We also noticed that MQANF (SEQ ID NO: 21)-tRNA$^{Phe}$ in the absence of the A-site ligand tends to dissociate slowly and introduced the respective drop-off reaction. Global fitting of the time courses using numerical integration yields a unique solution for the values of all rate constants (FIG. 2A,B). The step leading to the incorporation of the second Phe is slow, ~0.01 s$^{-1}$, compared to all translation steps, which are at least 10 times faster. MQANFF (SEQ ID NO: 26) peptides do not accumulate and are converted to the −1-frame peptide, MQANFFR (SEQ ID NO: 23). Thus, the incorporation of the second Phe residue is the rate-limiting step of frameshifting which commits the ribosome to the −1-frame translation.

In the presence of Leu-tRNA$^{Leu(UUA)}$, the ribosome synthesizes the 0-frame MQANF (SEQ ID NO: 21) peptide and then continues translation with Leu incorporation in the 0-frame or shifts into the −1-frame before Leu-tRNA$^{Leu(UUA)}$ can bind. If Leu is incorporated, the 0-frame MQANFL (SEQ ID NO: 27) product can partition between the 0-frame MQANFLG (SEQ ID NO: 22) and the −1-frame MQANFLR (SEQ ID NO: 24). Global fitting of the time courses gives well-defined rate constants for most of the steps (FIG. 2C-E). The rate-limiting step for the −1-frame FFR pathway has a rate constant of ~0.03 s$^{-1}$, similar to that for the isolated FFR pathway. The efficiency of the FFR pathway depends on the ratio between the rates of −1-slippage vs. Leu-tRNA$^{Leu(UUA)}$ binding. While the rate of slippage is constant, the rate of Leu-tRNA$^{Leu(UUA)}$ binding increases with concentration. This explains why addition of excess Leu-tRNA$^{Leu(UUA)}$ inhibits the FFR route. At high concentrations of Leu-tRNA$^{Leu(UUA)}$, the probability to bind Leu-tRNA$^{Leu(UUA)}$ to the A site is higher than to slip into the −1-frame. At this condition, the FFR pathway is suppressed and only the FLR pathway remains operational. After Leu incorporation, the −1FS efficiency of the FLR route is defined at the translocation step, because the partitioning between 0- and −1-frames takes place before decoding by Gly- and Arg-tRNAs (FIG. 1E). The ratio of the rate constants of Gly and Arg incorporation (0.53 s$^{-1}$ and 0.04 s$^{-1}$, respectively) gives the −1FS efficiency after Leu incorporation.

−1FS with Native Human Aa-tRNA

Our finding that a low-abundance Leu-tRNA$^{Leu(UUA)}$ isoacceptor controls the mechanism and efficiency of −1FS has prompted us to validate the key results using native aa-tRNA prepared directly from human cells, which should ensure the correct abundance and distribution of isoacceptors in the tRNA pool.

First, we analyzed the relative abundance of human Leu-tRNA$^{Leu}$ that reads the UUA codon (tRNA$^{Leu(UUA)}$) in total tRNA from different human cell types using qRT-PCR (FIG. 5). HIV-1 mainly infects CD4+T-lymphocytes and macrophages (Freed E. O. HIV-1 replication. Somat. Cell Mol. Genet. 2001; 26:13-33). We determined the ratio of Leu-tRNA$^{Leu(UUA)}$ to Leu-tRNA$^{Leu(CUG)}$ reading the most abundant Leu codon CUG. Leu-tRNA$^{Leu(UUA)}$ is 7-17-fold less abundant than Leu-tRNA$^{Leu(CUG)}$ in cell lines derived from T lymphocytes, and about 20-fold in HeLa cells, whereas in other types of human cells the ratio is about 1:3 (FIG. 5). The Leu-tRNA$^{Leu(UUA)}$ concentration varies by as much as 10-fold, whereas for Leu-tRNA$^{Leu(CUG)}$ the differences are smaller, except for HeLa cells, where the Leu-tRNA$^{Leu(CUG)}$ concentration is increased. As a control, we quantified the relative abundance of Val-tRNA$^{Val}$ isoacceptors reading a rare GUA codon and an abundant GUG codon. The tRNA$^{Val(GUA)}$ isoacceptor reading the rare codon is about 7-8 times less abundant than common tRNA$^{Val(GUG)}$, except for the 293T epithelial cells, where the amount of tRNA$^{Val(GUA)}$ is even lower (FIG. 5). Because the relative abundance of tRNA$^{Leu(UUA)}$ in HeLa cells is similar to that in cells used as a model for the HIV infection, we used total human tRNA purified from HeLa cells for the in vitro translation experiments described below.

Human aa-tRNA is active in translation when combined with EF-Tu and ribosomes from E. coli. The conformity of the human aa-tRNA to codon usage of eukaryotic mRNA was validated by translation of an mRNA coding for bovine γB-crystallin. The codon usage of γB-crystallin matches to the tRNA abundance of its eukaryotic host. With native human aa-tRNA, the native sequence of the γB-crystallin mRNA is translated efficiently. Introducing synonymous mutations in the mRNA that match the codon usage in E. coli, which is different from that in the eukaryotic host (Buhr et al. (2016). Mol Cell 61, 341-351), results in much less full-length product. This shows that the composition of the aa-tRNA pool indeed reflects the native codon usage of mRNAs from higher eukaryotes.

We then translated the gag-pol mRNA fragment encompassing the region from the nearest native (elongator) AUG codon of the gag mRNA upstream of the SS1, the SS1 with its downstream SL1 and the second putative frameshifting site pSS2 with a 32-nt downstream sequence, which is predicted to form a SL structure (pSL2) (FIG. 3A). To distinguish between the 0- and −1-frame translation products, we introduced a stop codon UAG in the 0-frame to obtain a 52 aa-long peptide; −1FS results into a 120 aa-long peptide product. To identify potential −2-frameshifting products, we mutated all native stop codons in the −2-frame downstream of the pSS2 (mRNA denoted as no-stop). Translation of no-stop mRNA leaves the product lengths in the 0- and −1-frames unchanged but additionally yields a 120-aa-long −2-frame product; despite their identical length, the −1-frame and −2-frame products have different electrophoretic mobility due to their different amino acid composition (FIG. 3B). The average rate of translation of the gag-pol or the native γB-crystallin mRNA is 0.5-0.7 aa/s, which is close to the range of translation rates measured in higher eukaryotes, 1-10 s$^{-1}$ (Ingolia et al. (2011). Cell 147, 789-802). Thus, the native human aa-tRNA preparation provides an authentic distribution of isoacceptor tRNAs to study translation of the HIV-1 gag-pol mRNA in vitro.

The −1FS efficiency of the native gap-pol frameshifting sequence is 6-7% (FIG. 3C-E). Formation of 0-frame and −1-frame products starts after a 30 s delay which may be caused by an early translational pausing event (appearing as a prominent peptide band between 7 s to 30 s of translation (FIG. 3B,C). In contrast, the −2-frame product appears after a significantly longer delay of 120 s. At this time, synthesis of the 0-frame product is finished on the majority of ribosomes (FIG. 3B), suggesting that −2FS may arise due to a fraction of ribosomes that undergo long translation pausing. Addition of exogenous Leu-tRNA$^{Leu(UUA)}$ decreases the −1FS efficiency to 4% (FIG. 3D). A similarly reduced FS efficiency is observed when the UUA codon is mutated to UUC, which does not interrupt the slippery run of six Us, but changes the identity of the tRNA reading the second slippery codon to the abundant tRNA$^{Phe}$ (FIG. 3E). Thus, reassigning the second codon of the slippery site to an abundant tRNA has the same effect as adding excess of tRNA$^{(UUA)}$ to the native sequence. Shortening the slippery site to four Us decreased FS to 2%. Disrupting SS1 alone or together with pSS2 diminishes the FS efficiency to about 1%, which is the background level of these experiments (FIG. 3E).

We also tested whether addition of Leu-tRNA$^{Leu(UUA)}$ alters the frameshifting efficiency in a homologous recon-stituted mammalian translation system. Ribosomal subunits (40S and 60S), initiation factors (eIF1A, eIF1, eIF2, eIF3, eIF4A, eIF4B, eIF5, and eIF5B) and Met-tRNA$_i$ were used to form the 80S initiation complex on an mRNA with an unstructured 5'UTR coding for the SS1 and the SL1 frag-ment of HIV-1. To synthesize the 0-frame MVANFLG (SEQ ID NO: 33) and the –1-frame MVANFLR (SEQ ID NO: 34) peptides, we used the tRNA from HeLa cells aminoacylated with a mixture of the required amino acids with or without Leu; incorporation of the –1-frame Arg was monitored by the HPLC analysis. As controls, we included the mRNA coding for MVANFLR (SEQ ID NO: 34) in 0-frame (–1-frame control), which provides the estimate for the maxi-mum Arg incorporation, and the mRNA without the SS1 but with SL1 (0-frame control). The –1FS efficiency in this fully reconstituted eukaryotic translation system is about 20-25% in the presence of native amounts of tRNA$^{Leu(UUA)}$ (FIG. 6A). When leucine was omitted from the aminoacylation mixture, the –1FS efficiency increases to 40% (FIG. 6B). Thus, Leu-tRNA$^{Leu(UUA)}$ modulates –1FS efficiency on HIV mRNA also in the homologous mammalian translation sys-tem.

Finally, we tested whether tRNA$^{Leu(UUA)}$ can also modu-late frameshifting in *alphaviruses*. In gene 6K of the alpha-virus SFV –1FS defines the ratio between two structural proteins, 6K (0-frame) and TransFrame (TF, –1-frame), which play a role in the envelope protein processing, mem-brane permeabilization, virion assembly, virus budding, and contribute to infectivity. The efficiency of –1FS in SFV measured with dual-luciferase reporters in human cells is about 15% (Firth, A. E., Chung, B. Y., Fleeton, M. N. and Atkins, J. F. (2008). Discovery of frameshifting in Alpha-virus 6K resolves a 20-year enigma. Virol J 5, 108). –1FS in SFV can result in two peptides, FFS and FLS, depending on the presence of the Leu-tRNA$^{Leu(UUA)}$ isoacceptor (FIG. 7A). In the absence of Leu-tRNA$^{Leu(UUA)}$, the FFS product is formed and its yield depends on the concentration of Phe-tRNA$^{Phe}$ (FIG. 7B), suggesting that the slippage occurs prior to and independent of tRNA$^{Leu(UUA)}$ incorporation, similarly to "hungry" slippage in HIV-1. With the increase in Leu-tRNA$^{Leu(UUA)}$ concentration, the –1FS efficiency decreases dramatically from about 70% in the absence of tRNA$^{Leu(UUA)}$ to 18% at tRNA$^{Leu(UUA)}$ saturation (FIG. 7C). Thus, the FFS route in SFV is operational when tRNA$^{Leu(UUA)}$ is absent or in limited supply, whereas under saturating translation conditions the FLS route becomes prevalent.

---

The invention claimed is:

1. A method of treating or ameliorating an infection with HIV virus, with SIV virus, with an Alphavirus and/or AIDS in a subject, said method comprising administering a tRNALeu(UAA) which (a) differs from any human wild-type tRNALeu(UAA), by at least one up to ten mutations of the base sequence in a stem region of the tRNA, wherein each of said mutations is a substitution or deletion; and/or (b) comprises at least one modification of a ribose and/or of a phosphate, wherein said modification is selected from 2'-O-methyl, 2'-deoxy, 2'-fluoro, thiophosphate, LNA, and PNA.

2. The method of claim 1, wherein said subject is a human.

3. The method of claim 1, wherein the tRNALeu(UAA), consists of the sequence of SEQ ID NO: 1 or 2.

* * * * *

SEQUENCE LISTING

<160> NUMBER OF SEQ ID NOS: 50

<210> SEQ ID NO 1
<211> LENGTH: 86
<212> TYPE: RNA
<213> ORGANISM: Homo sapiens
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (6)..(7)
<223> OTHER INFORMATION: n is a, c, g, or u
<220> FEATURE:
<221> NAME/KEY: misc_feature
<222> LOCATION: (16)..(16)
<223> OTHER INFORMATION: n is a, c, g, or u
<220> FEATURE:
<221> NAME/KEY: misc_feature
<222> LOCATION: (27)..(32)
<223> OTHER INFORMATION: n is a, c, g, or u
<220> FEATURE:
<221> NAME/KEY: misc_feature
<222> LOCATION: (38)..(43)
<223> OTHER INFORMATION: n is a, c, g, or u
<220> FEATURE:
<221> NAME/KEY: misc_feature
<222> LOCATION: (45)..(50)
<223> OTHER INFORMATION: n is a, c, g, or u
<220> FEATURE:
<221> NAME/KEY: misc_feature
<222> LOCATION: (52)..(52)
<223> OTHER INFORMATION: n is a, c, g, or u
<220> FEATURE:
<221> NAME/KEY: misc_feature
<222> LOCATION: (54)..(56)
<223> OTHER INFORMATION: n is a, c, g, or u
<220> FEATURE:
<221> NAME/KEY: misc_feature
<222> LOCATION: (70)..(70)
<223> OTHER INFORMATION: n is a, c, g, or u -continued

```
<220> FEATURE:
<221> NAME/KEY: misc_feature
<222> LOCATION: (76)..(77)
<223> OTHER INFORMATION: n is a, c, g, or u
<220> FEATURE:
<221> NAME/KEY: misc_feature
<222> LOCATION: (81)..(82)
<223> OTHER INFORMATION: n is a, c, g, or u

<400> SEQUENCE: 1
nnnagnnugg ccgagngguu aaggcgnnnn nnuuaagnnn nnnunnnnnn angnnngcgu      60
ggguucgaan cccacnncug nnacca                                         86

<210> SEQ ID NO 2
<211> LENGTH: 86
<212> TYPE: RNA
<213> ORGANISM: Homo sapiens

<400> SEQUENCE: 2
accaggaugg ccgagugguu aaggcguugg acuuaagauc caauggacau auguccgcgu      60
ggguucgaac cccacuccug guacca                                         86

<210> SEQ ID NO 3
<211> LENGTH: 83
<212> TYPE: RNA
<213> ORGANISM: Homo sapiens
<220> FEATURE:
<221> NAME/KEY: modified_base
<222> LOCATION: (8)..(8)
<223> OTHER INFORMATION: Thymine
<220> FEATURE:
<221> NAME/KEY: modified_base
<222> LOCATION: (16)..(16)
<223> OTHER INFORMATION: Thymine
<220> FEATURE:
<221> NAME/KEY: modified_base
<222> LOCATION: (16)..(16)
<223> OTHER INFORMATION: Thymine
<220> FEATURE:
<221> NAME/KEY: modified_base
<222> LOCATION: (19)..(20)
<223> OTHER INFORMATION: Thymine
<220> FEATURE:
<221> NAME/KEY: modified_base
<222> LOCATION: (27)..(28)
<223> OTHER INFORMATION: Thymine
<220> FEATURE:
<221> NAME/KEY: modified_base
<222> LOCATION: (33)..(34)
<223> OTHER INFORMATION: Thymine
<220> FEATURE:
<221> NAME/KEY: modified_base
<222> LOCATION: (39)..(39)
<223> OTHER INFORMATION: Thymine
<220> FEATURE:
<221> NAME/KEY: modified_base
<222> LOCATION: (44)..(44)
<223> OTHER INFORMATION: Thymine
<220> FEATURE:
<221> NAME/KEY: modified_base
<222> LOCATION: (50)..(50)
<223> OTHER INFORMATION: Thymine
<220> FEATURE:
<221> NAME/KEY: modified_base
<222> LOCATION: (52)..(52)
<223> OTHER INFORMATION: Thymine
<220> FEATURE:
<221> NAME/KEY: modified_base
<222> LOCATION: (54)..(54)
<223> OTHER INFORMATION: Thymine
<220> FEATURE:
<221> NAME/KEY: modified_base
<222> LOCATION: (60)..(60)
```

```
<223> OTHER INFORMATION: Thymine
<220> FEATURE:
<221> NAME/KEY: modified_base
<222> LOCATION: (64)..(65)
<223> OTHER INFORMATION: Thymine
<220> FEATURE:
<221> NAME/KEY: modified_base
<222> LOCATION: (76)..(76)
<223> OTHER INFORMATION: Thymine
<220> FEATURE:
<221> NAME/KEY: modified_base
<222> LOCATION: (79)..(79)
<223> OTHER INFORMATION: Thymine
<220> FEATURE:
<221> NAME/KEY: modified_base
<222> LOCATION: (82)..(82)
<223> OTHER INFORMATION: Thymine

<400> SEQUENCE: 3
accaggaugg ccgagugguu aaggcguugg acuuaagauc caauggacau auguccgcgu        60
ggguucgaac cccacuccug gua                                              83

<210> SEQ ID NO 4
<211> LENGTH: 83
<212> TYPE: RNA
<213> ORGANISM: Homo sapiens
<220> FEATURE:
<221> NAME/KEY: modified_base
<222> LOCATION: (8)..(8)
<223> OTHER INFORMATION: Thymine
<220> FEATURE:
<221> NAME/KEY: modified_base
<222> LOCATION: (16)..(16)
<223> OTHER INFORMATION: Thymine
<220> FEATURE:
<221> NAME/KEY: modified_base
<222> LOCATION: (19)..(20)
<223> OTHER INFORMATION: Thymine
<220> FEATURE:
<221> NAME/KEY: modified_base
<222> LOCATION: (27)..(28)
<223> OTHER INFORMATION: Thymine
<220> FEATURE:
<221> NAME/KEY: modified_base
<222> LOCATION: (33)..(34)
<223> OTHER INFORMATION: Thymine
<220> FEATURE:
<221> NAME/KEY: modified_base
<222> LOCATION: (39)..(39)
<223> OTHER INFORMATION: Thymine
<220> FEATURE:
<221> NAME/KEY: modified_base
<222> LOCATION: (44)..(44)
<223> OTHER INFORMATION: Thymine
<220> FEATURE:
<221> NAME/KEY: modified_base
<222> LOCATION: (49)..(49)
<223> OTHER INFORMATION: Thymine
<220> FEATURE:
<221> NAME/KEY: modified_base
<222> LOCATION: (52)..(52)
<223> OTHER INFORMATION: Thymine
<220> FEATURE:
<221> NAME/KEY: modified_base
<222> LOCATION: (60)..(60)
<223> OTHER INFORMATION: Thymine
<220> FEATURE:
<221> NAME/KEY: modified_base
<222> LOCATION: (64)..(65)
<223> OTHER INFORMATION: Thymine
<220> FEATURE:
<221> NAME/KEY: modified_base
<222> LOCATION: (76)..(76)
<223> OTHER INFORMATION: Thymine
<220> FEATURE:
<221> NAME/KEY: modified_base
```

```
<222> LOCATION: (78)..(78)
<223> OTHER INFORMATION: Thymine
<220> FEATURE:
<221> NAME/KEY: modified_base
<222> LOCATION: (82)..(82)
<223> OTHER INFORMATION: Thymine

<400> SEQUENCE: 4
accgggaugg ccgagugguu aaggcguugg acuuaagauc caaugggcug gugcccgcgu          60
ggguucgaac cccacucucg gua                                                  83

<210> SEQ ID NO 5
<211> LENGTH: 83
<212> TYPE: RNA
<213> ORGANISM: Homo sapiens
<220> FEATURE:
<221> NAME/KEY: modified_base
<222> LOCATION: (8)..(8)
<223> OTHER INFORMATION: Thymine
<220> FEATURE:
<221> NAME/KEY: modified_base
<222> LOCATION: (16)..(16)
<223> OTHER INFORMATION: Thymine
<220> FEATURE:
<221> NAME/KEY: modified_base
<222> LOCATION: (19)..(20)
<223> OTHER INFORMATION: Thymine
<220> FEATURE:
<221> NAME/KEY: modified_base
<222> LOCATION: (27)..(28)
<223> OTHER INFORMATION: Thymine
<220> FEATURE:
<221> NAME/KEY: modified_base
<222> LOCATION: (33)..(34)
<223> OTHER INFORMATION: Thymine
<220> FEATURE:
<221> NAME/KEY: modified_base
<222> LOCATION: (39)..(39)
<223> OTHER INFORMATION: Thymine
<220> FEATURE:
<221> NAME/KEY: modified_base
<222> LOCATION: (44)..(44)
<223> OTHER INFORMATION: Thymine
<220> FEATURE:
<221> NAME/KEY: modified_base
<222> LOCATION: (48)..(49)
<223> OTHER INFORMATION: Thymine
<220> FEATURE:
<221> NAME/KEY: modified_base
<222> LOCATION: (52)..(52)
<223> OTHER INFORMATION: Thymine
<220> FEATURE:
<221> NAME/KEY: modified_base
<222> LOCATION: (54)..(54)
<223> OTHER INFORMATION: Thymine
<220> FEATURE:
<221> NAME/KEY: modified_base
<222> LOCATION: (60)..(60)
<223> OTHER INFORMATION: Thymine
<220> FEATURE:
<221> NAME/KEY: modified_base
<222> LOCATION: (64)..(65)
<223> OTHER INFORMATION: Thymine
<220> FEATURE:
<221> NAME/KEY: modified_base
<222> LOCATION: (76)..(77)
<223> OTHER INFORMATION: Thymine
<220> FEATURE:
<221> NAME/KEY: modified_base
<222> LOCATION: (79)..(79)
<223> OTHER INFORMATION: Thymine
<220> FEATURE:
<221> NAME/KEY: modified_base
<222> LOCATION: (82)..(82)
<223> OTHER INFORMATION: Thymine
```

-continued

```
<400> SEQUENCE: 5
accagaaugg ccgagugguu aaggcguugg acuuaagauc caauggauuc auauccgcgu      60
ggguucgaac cccacuucug gua                                             83

<210> SEQ ID NO 6
<211> LENGTH: 83
<212> TYPE: RNA
<213> ORGANISM: Homo sapiens
<220> FEATURE:
<221> NAME/KEY: modified_base
<222> LOCATION: (8)..(8)
<223> OTHER INFORMATION: Thymine
<220> FEATURE:
<221> NAME/KEY: modified_base
<222> LOCATION: (12)..(12)
<223> OTHER INFORMATION: Thymine
<220> FEATURE:
<221> NAME/KEY: modified_base
<222> LOCATION: (16)..(16)
<223> OTHER INFORMATION: Thymine
<220> FEATURE:
<221> NAME/KEY: modified_base
<222> LOCATION: (19)..(20)
<223> OTHER INFORMATION: Thymine
<220> FEATURE:
<221> NAME/KEY: modified_base
<222> LOCATION: (27)..(28)
<223> OTHER INFORMATION: Thymine
<220> FEATURE:
<221> NAME/KEY: modified_base
<222> LOCATION: (33)..(34)
<223> OTHER INFORMATION: Thymine
<220> FEATURE:
<221> NAME/KEY: modified_base
<222> LOCATION: (39)..(39)
<223> OTHER INFORMATION: Thymine
<220> FEATURE:
<221> NAME/KEY: modified_base
<222> LOCATION: (44)..(44)
<223> OTHER INFORMATION: Thymine
<220> FEATURE:
<221> NAME/KEY: modified_base
<222> LOCATION: (52)..(52)
<223> OTHER INFORMATION: Thymine
<220> FEATURE:
<221> NAME/KEY: modified_base
<222> LOCATION: (54)..(54)
<223> OTHER INFORMATION: Thymine
<220> FEATURE:
<221> NAME/KEY: modified_base
<222> LOCATION: (60)..(60)
<223> OTHER INFORMATION: Thymine
<220> FEATURE:
<221> NAME/KEY: modified_base
<222> LOCATION: (64)..(65)
<223> OTHER INFORMATION: Thymine
<220> FEATURE:
<221> NAME/KEY: modified_base
<222> LOCATION: (76)..(76)
<223> OTHER INFORMATION: Thymine
<220> FEATURE:
<221> NAME/KEY: modified_base
<222> LOCATION: (82)..(82)
<223> OTHER INFORMATION: Thymine

<400> SEQUENCE: 6
accgggaugg cugagugguu aaggcguugg acuuaagauc caauggacag guguccgcgu      60
ggguucgagc cccacucccg gua                                             83

<210> SEQ ID NO 7
<211> LENGTH: 83
<212> TYPE: RNA
<213> ORGANISM: Homo sapiens
```

-continued

```
<220> FEATURE:
<221> NAME/KEY: modified_base
<222> LOCATION: (3)..(3)
<223> OTHER INFORMATION: Thymine
<220> FEATURE:
<221> NAME/KEY: modified_base
<222> LOCATION: (6)..(8)
<223> OTHER INFORMATION: Thymine
<220> FEATURE:
<221> NAME/KEY: modified_base
<222> LOCATION: (12)..(12)
<223> OTHER INFORMATION: Thymine
<220> FEATURE:
<221> NAME/KEY: modified_base
<222> LOCATION: (16)..(16)
<223> OTHER INFORMATION: Thymine
<220> FEATURE:
<221> NAME/KEY: modified_base
<222> LOCATION: (19)..(20)
<223> OTHER INFORMATION: Thymine
<220> FEATURE:
<221> NAME/KEY: modified_base
<222> LOCATION: (27)..(28)
<223> OTHER INFORMATION: Thymine
<220> FEATURE:
<221> NAME/KEY: modified_base
<222> LOCATION: (33)..(34)
<223> OTHER INFORMATION: Thymine
<220> FEATURE:
<221> NAME/KEY: modified_base
<222> LOCATION: (39)..(39)
<223> OTHER INFORMATION: Thymine
<220> FEATURE:
<221> NAME/KEY: modified_base
<222> LOCATION: (44)..(44)
<223> OTHER INFORMATION: Thymine
<220> FEATURE:
<221> NAME/KEY: modified_base
<222> LOCATION: (49)..(49)
<223> OTHER INFORMATION: Thymine
<220> FEATURE:
<221> NAME/KEY: modified_base
<222> LOCATION: (52)..(52)
<223> OTHER INFORMATION: Thymine
<220> FEATURE:
<221> NAME/KEY: modified_base
<222> LOCATION: (56)..(56)
<223> OTHER INFORMATION: Thymine
<220> FEATURE:
<221> NAME/KEY: modified_base
<222> LOCATION: (58)..(58)
<223> OTHER INFORMATION: Thymine
<220> FEATURE:
<221> NAME/KEY: modified_base
<222> LOCATION: (60)..(60)
<223> OTHER INFORMATION: Thymine
<220> FEATURE:
<221> NAME/KEY: modified_base
<222> LOCATION: (64)..(66)
<223> OTHER INFORMATION: Thymine
<220> FEATURE:
<221> NAME/KEY: modified_base
<222> LOCATION: (76)..(76)
<223> OTHER INFORMATION: Thymine
<220> FEATURE:
<221> NAME/KEY: modified_base
<222> LOCATION: (79)..(79)
<223> OTHER INFORMATION: Thymine
<220> FEATURE:
<221> NAME/KEY: modified_base
<222> LOCATION: (82)..(82)
<223> OTHER INFORMATION: Thymine

<400> SEQUENCE: 7
acucauuugg cugagugguu aaggcauugg acuuaagauc caauggagua guggcugugu      60
ggguuuaaac cccacuacug gua                                             83
```

-continued

```
<210> SEQ ID NO 8
<211> LENGTH: 69
<212> TYPE: RNA
<213> ORGANISM: Homo sapiens
<220> FEATURE:
<221> NAME/KEY: modified_base
<222> LOCATION: (8)..(8)
<223> OTHER INFORMATION: Thymine
<220> FEATURE:
<221> NAME/KEY: modified_base
<222> LOCATION: (11)..(11)
<223> OTHER INFORMATION: Thymine
<220> FEATURE:
<221> NAME/KEY: modified_base
<222> LOCATION: (14)..(14)
<223> OTHER INFORMATION: Thymine
<220> FEATURE:
<221> NAME/KEY: modified_base
<222> LOCATION: (17)..(18)
<223> OTHER INFORMATION: Thymine
<220> FEATURE:
<221> NAME/KEY: modified_base
<222> LOCATION: (25)..(26)
<223> OTHER INFORMATION: Thymine
<220> FEATURE:
<221> NAME/KEY: modified_base
<222> LOCATION: (30)..(31)
<223> OTHER INFORMATION: Thymine
<220> FEATURE:
<221> NAME/KEY: modified_base
<222> LOCATION: (40)..(43)
<223> OTHER INFORMATION: Thymine
<220> FEATURE:
<221> NAME/KEY: modified_base
<222> LOCATION: (50)..(51)
<223> OTHER INFORMATION: Thymine
<220> FEATURE:
<221> NAME/KEY: modified_base
<222> LOCATION: (55)..(56)
<223> OTHER INFORMATION: Thymine
<220> FEATURE:
<221> NAME/KEY: modified_base
<222> LOCATION: (59)..(60)
<223> OTHER INFORMATION: Thymine
<220> FEATURE:
<221> NAME/KEY: modified_base
<222> LOCATION: (63)..(65)
<223> OTHER INFORMATION: Thymine
<220> FEATURE:
<221> NAME/KEY: modified_base
<222> LOCATION: (67)..(67)
<223> OTHER INFORMATION: Thymine
<220> FEATURE:
<221> NAME/KEY: modified_base
<222> LOCATION: (69)..(69)
<223> OTHER INFORMATION: Thymine

<400> SEQUENCE: 8
gagaaaguca ucguaguuac gaaguuggcu uaaacccagu uuugggaggu ucaauuccuu      60
ccuuucucu                                                             69

<210> SEQ ID NO 9
<211> LENGTH: 84
<212> TYPE: RNA
<213> ORGANISM: Homo sapiens
<220> FEATURE:
<221> NAME/KEY: modified_base
<222> LOCATION: (8)..(8)
<223> OTHER INFORMATION: Thymine
<220> FEATURE:
<221> NAME/KEY: modified_base
<222> LOCATION: (16)..(16)
<223> OTHER INFORMATION: Thymine
<220> FEATURE:
<221> NAME/KEY: modified_base
```

```
<222> LOCATION: (19)..(20)
<223> OTHER INFORMATION: Thymine
<220> FEATURE:
<221> NAME/KEY: modified_base
<222> LOCATION: (29)..(29)
<223> OTHER INFORMATION: Thymine
<220> FEATURE:
<221> NAME/KEY: modified_base
<222> LOCATION: (34)..(35)
<223> OTHER INFORMATION: Thymine
<220> FEATURE:
<221> NAME/KEY: modified_base
<222> LOCATION: (45)..(45)
<223> OTHER INFORMATION: Thymine
<220> FEATURE:
<221> NAME/KEY: modified_base
<222> LOCATION: (51)..(51)
<223> OTHER INFORMATION: Thymine
<220> FEATURE:
<221> NAME/KEY: modified_base
<222> LOCATION: (53)..(53)
<223> OTHER INFORMATION: Thymine
<220> FEATURE:
<221> NAME/KEY: modified_base
<222> LOCATION: (55)..(55)
<223> OTHER INFORMATION: Thymine
<220> FEATURE:
<221> NAME/KEY: modified_base
<222> LOCATION: (57)..(57)
<223> OTHER INFORMATION: Thymine
<220> FEATURE:
<221> NAME/KEY: modified_base
<222> LOCATION: (59)..(59)
<223> OTHER INFORMATION: Thymine
<220> FEATURE:
<221> NAME/KEY: modified_base
<222> LOCATION: (61)..(61)
<223> OTHER INFORMATION: Thymine
<220> FEATURE:
<221> NAME/KEY: modified_base
<222> LOCATION: (65)..(67)
<223> OTHER INFORMATION: Thymine
<220> FEATURE:
<221> NAME/KEY: modified_base
<222> LOCATION: (77)..(77)
<223> OTHER INFORMATION: Thymine
<220> FEATURE:
<221> NAME/KEY: modified_base
<222> LOCATION: (80)..(80)
<223> OTHER INFORMATION: Thymine
<220> FEATURE:
<221> NAME/KEY: modified_base
<222> LOCATION: (83)..(83)
<223> OTHER INFORMATION: Thymine

<400> SEQUENCE: 9
accaggaugg ccaaguaguu aaaggcacug gacuuaagag ccaauggaca uaugucugug        60
uggguuugaa ccccacuccu ggug                                               84

<210> SEQ ID NO 10
<211> LENGTH: 75
<212> TYPE: RNA
<213> ORGANISM: Homo sapiens
<220> FEATURE:
<221> NAME/KEY: modified_base
<222> LOCATION: (2)..(3)
<223> OTHER INFORMATION: Thymine
<220> FEATURE:
<221> NAME/KEY: modified_base
<222> LOCATION: (8)..(8)
<223> OTHER INFORMATION: Thymine
<220> FEATURE:
<221> NAME/KEY: modified_base
<222> LOCATION: (18)..(18)
<223> OTHER INFORMATION: Thymine
<220> FEATURE:
```

```
<221> NAME/KEY: modified_base
<222> LOCATION: (21)..(21)
<223> OTHER INFORMATION: Thymine
<220> FEATURE:
<221> NAME/KEY: modified_base
<222> LOCATION: (24)..(25)
<223> OTHER INFORMATION: Thymine
<220> FEATURE:
<221> NAME/KEY: modified_base
<222> LOCATION: (29)..(29)
<223> OTHER INFORMATION: Thymine
<220> FEATURE:
<221> NAME/KEY: modified_base
<222> LOCATION: (35)..(36)
<223> OTHER INFORMATION: Thymine
<220> FEATURE:
<221> NAME/KEY: modified_base
<222> LOCATION: (41)..(44)
<223> OTHER INFORMATION: Thymine
<220> FEATURE:
<221> NAME/KEY: modified_base
<222> LOCATION: (46)..(46)
<223> OTHER INFORMATION: Thymine
<220> FEATURE:
<221> NAME/KEY: modified_base
<222> LOCATION: (49)..(49)
<223> OTHER INFORMATION: Thymine
<220> FEATURE:
<221> NAME/KEY: modified_base
<222> LOCATION: (56)..(57)
<223> OTHER INFORMATION: Thymine
<220> FEATURE:
<221> NAME/KEY: modified_base
<222> LOCATION: (62)..(62)
<223> OTHER INFORMATION: Thymine
<220> FEATURE:
<221> NAME/KEY: modified_base
<222> LOCATION: (65)..(65)
<223> OTHER INFORMATION: Thymine
<220> FEATURE:
<221> NAME/KEY: modified_base
<222> LOCATION: (67)..(68)
<223> OTHER INFORMATION: Thymine
<220> FEATURE:
<221> NAME/KEY: modified_base
<222> LOCATION: (70)..(71)
<223> OTHER INFORMATION: Thymine

<400> SEQUENCE: 10
guuaagaugg cagagccugg uaauugcaua aaacuuaaaa uuuuauaauc agagguucaa        60
cuccucuucu uaaca                                                        75

<210> SEQ ID NO 11
<211> LENGTH: 75
<212> TYPE: RNA
<213> ORGANISM: Homo sapiens
<220> FEATURE:
<221> NAME/KEY: modified_base
<222> LOCATION: (2)..(3)
<223> OTHER INFORMATION: Thymine
<220> FEATURE:
<221> NAME/KEY: modified_base
<222> LOCATION: (8)..(8)
<223> OTHER INFORMATION: Thymine
<220> FEATURE:
<221> NAME/KEY: modified_base
<222> LOCATION: (24)..(25)
<223> OTHER INFORMATION: Thymine
<220> FEATURE:
<221> NAME/KEY: modified_base
<222> LOCATION: (29)..(29)
<223> OTHER INFORMATION: Thymine
<220> FEATURE:
<221> NAME/KEY: modified_base
<222> LOCATION: (35)..(36)
<223> OTHER INFORMATION: Thymine
```

```
<220> FEATURE:
<221> NAME/KEY: modified_base
<222> LOCATION: (42)..(44)
<223> OTHER INFORMATION: Thymine
<220> FEATURE:
<221> NAME/KEY: modified_base
<222> LOCATION: (46)..(46)
<223> OTHER INFORMATION: Thymine
<220> FEATURE:
<221> NAME/KEY: modified_base
<222> LOCATION: (49)..(49)
<223> OTHER INFORMATION: Thymine
<220> FEATURE:
<221> NAME/KEY: modified_base
<222> LOCATION: (56)..(57)
<223> OTHER INFORMATION: Thymine
<220> FEATURE:
<221> NAME/KEY: modified_base
<222> LOCATION: (62)..(62)
<223> OTHER INFORMATION: Thymine
<220> FEATURE:
<221> NAME/KEY: modified_base
<222> LOCATION: (65)..(65)
<223> OTHER INFORMATION: Thymine
<220> FEATURE:
<221> NAME/KEY: modified_base
<222> LOCATION: (67)..(67)
<223> OTHER INFORMATION: Thymine
<220> FEATURE:
<221> NAME/KEY: modified_base
<222> LOCATION: (70)..(71)
<223> OTHER INFORMATION: Thymine

<400> SEQUENCE: 11
guuaagaugg cagagcccgg caauugcaua agacuuaaaa cuuuauaauc agagguucaa      60
cuccucucau uaaca                                                       75

<210> SEQ ID NO 12
<211> LENGTH: 142
<212> TYPE: RNA
<213> ORGANISM: Artificial Sequence
<220> FEATURE:
<223> OTHER INFORMATION: wt short mRNA HPLC

<400> SEQUENCE: 12
gggagaccgg aauucgagcu cgcccaaacg cgguuggauu ccugaugaaa aguucuauga      60 ggguguauaau gcaggcuaau uuuuuaggga agaucuggcc uuccuacaag ggaaggccag     120
ggaauuuucu ucagagcaga cc                                              142

<210> SEQ ID NO 13
<211> LENGTH: 142
<212> TYPE: RNA
<213> ORGANISM: Artificial Sequence
<220> FEATURE:
<223> OTHER INFORMATION: U4C mRNA HPLC

<400> SEQUENCE: 13
gggagaccgg aauucgagcu cgcccaaacg cgguuggauu ccugaugaaa aguucuauga      60 ggguguauaau gcaggcuaau uucuuaggga agaucuggcc uuccuacaag ggaaggccag     120
ggaauuuucu ucagagcaga cc                                              142

<210> SEQ ID NO 14
<211> LENGTH: 142
<212> TYPE: RNA
<213> ORGANISM: Artificial Sequence
<220> FEATURE:
<223> OTHER INFORMATION: 2 / +1 mRNA HPLC
```

-continued

```
<400> SEQUENCE: 14
gggagaccgg aauucgagcu cgcccaaacg cgguuggauu ccugaugaaa aguucuauga          60 ggguguauaau gcaggcuaau uuuuuaugga agaucuggcc uuccuacaag ggaaggccag         120
ggaauuuucu ucagagcaga cc                                                  142

<210> SEQ ID NO 15
<211> LENGTH: 428
<212> TYPE: RNA
<213> ORGANISM: Artificial Sequence
<220> FEATURE:
<223> OTHER INFORMATION: wt long mRNA gel

<400> SEQUENCE: 15
gggagaccgg aauucgagcu cgcccaaacg cgguuggauu ccugaugaaa aguucuauga          60 ggguguauaau gaaagauugu acugagagac aggcuaauuu uuuagggaag aucuggccuu        120
ccuacaaggg aaggccaggg aauuuucuuc agagcagacc agagccaaca gccccaccag         180
aagagagcuu caggucuggg guagagacaa caacuccccc ucaguagcag gagccgauag         240
acaaggaacu guauccuuua acuucccuca ggucacucuu uggcaacgac cccucgucac         300
aauaaagaua gggggggcaac uaaaggaagc ucuauuagau acaggagcag augauacagu        360
auuagaagaa augaguuugc caggaagaug gaaaccaaaa augauagggg gaauuggagg         420
uuuuuauca                                                                 428

<210> SEQ ID NO 16
<211> LENGTH: 428
<212> TYPE: RNA
<213> ORGANISM: Artificial Sequence
<220> FEATURE:
<223> OTHER INFORMATION: 0-frame control mRNA gel

<400> SEQUENCE: 16
gggagaccgg aauucgagcu cgcccaaacg cgguuggauu ccugaugaaa aguucuauga          60 ggguguauaau gaaagauugu acugagagac aggcuaacuu cguagggaag aucuggccuu        120
ccuacaaggg aaggccaggg aauuuccuuc agagcagacc agagccaaca gccccaccag         180
aagagagcuu caggucuggg guagagacaa caacuccccc ucaguagcag gagccgauag         240
acaaggaacu guauccuuua acuucccuca ggucacucuu uggcaacgac cccucgucac         300
aauaaagaua gggggggcaac uaaaggaagc ucuauuagau acaggagcag augauacagu        360
auuagaagaa augaguuugc caggaagaug gaaaccaaaa augauagggg gaauuggagg         420
uuuuuauca                                                                 428

<210> SEQ ID NO 17
<211> LENGTH: 429
<212> TYPE: RNA
<213> ORGANISM: Artificial Sequence
<220> FEATURE:
<223> OTHER INFORMATION: 1-frame control mRNA gel

<400> SEQUENCE: 17
gggagaccgg aauucgagcu cgcccaaacg cgguuggauu ccugaugaaa aguucuauga          60 ggguguauaau gaaagauugu acugagagac aggcuaacuu cguaagggaa gaucuggccu        120
uccuacaagg gaaggccagg gaauuuccuu cagagcagac cagagccaac agccccacca        180
gaagagagcu ucaggucugg gguagagaca acaacucccc ucaguagca ggagccgaua         240 gacaaggaac uguauccuuu aacuucccuc aggucacucu uuggcaacga ccccucguca        300
```

-continued

```
caauaaagau aggggggcaa cuaaaggaag cucuauuaga uacaggagca gaugauacag      360
uauuagaaga aaugaguuug ccaggaagau ggaaaccaaa aaugauaggg ggaauuggag      420
guuuuauca                                                              429

<210> SEQ ID NO 18
<211> LENGTH: 430
<212> TYPE: RNA
<213> ORGANISM: Artificial Sequence
<220> FEATURE:
<223> OTHER INFORMATION: 2-frame control mRNA gel

<400> SEQUENCE: 18
gggagaccgg aauucgagcu cgcccaaacg cgguuggauu ccugaugaaa aguucuauga       60 ggguguauaau gaaagauugu acugagagac aggcuaacuu cguaagggaa gaucuggccu      120
uccuacaagg gaaggccagg gaauuuccuu ucagagcaga ccagagccaa cagccccacc      180
agaagagagc uucaggucug gggucgagac aacaacuccc ccucaguagc aggagccgau      240
cgacaaggaa cuguauccuu ucacuucccu caggucacuc uuuggcaacg accccucguc      300
acaauaaaga uagggggggca acuaaaggaa gcucuauuag auacaggagc agaucauaca      360
guauuagaag aaaugaguuu gccaggaaga uggaaaccaa aaaugauagg gggaauugga      420
gguuuuauca                                                             430

<210> SEQ ID NO 19
<211> LENGTH: 33
<212> TYPE: RNA
<213> ORGANISM: Artificial Sequence
<220> FEATURE:
<223> OTHER INFORMATION: fM-F-R(AGG)-Stop

<400> SEQUENCE: 19
guuaacaggu auacauacua uguucaggau uac                                     33

<210> SEQ ID NO 20
<211> LENGTH: 33
<212> TYPE: RNA
<213> ORGANISM: Artificial Sequence
<220> FEATURE:
<223> OTHER INFORMATION: fM-L-R(AGG)-Stop

<400> SEQUENCE: 20
guuaacaggu auacauacua uguuaaggau uac                                     33

<210> SEQ ID NO 21
<211> LENGTH: 5
<212> TYPE: PRT
<213> ORGANISM: Artificial Sequence
<220> FEATURE:
<223> OTHER INFORMATION: -1-frame peptide

<400> SEQUENCE: 21

Met Gln Ala Asn Phe
1               5

<210> SEQ ID NO 22
<211> LENGTH: 7
<212> TYPE: PRT
<213> ORGANISM: Artificial Sequence
<220> FEATURE:
<223> OTHER INFORMATION: 0-frame peptide

<400> SEQUENCE: 22
```

```
Met Gln Ala Asn Phe Leu Gly
1               5

<210> SEQ ID NO 23
<211> LENGTH: 7
<212> TYPE: PRT
<213> ORGANISM: Artificial Sequence
<220> FEATURE:
<223> OTHER INFORMATION: 1-frame peptide

<400> SEQUENCE: 23

Met Gln Ala Asn Phe Phe Arg
1               5

<210> SEQ ID NO 24
<211> LENGTH: 7
<212> TYPE: PRT
<213> ORGANISM: Artificial Sequence
<220> FEATURE:
<223> OTHER INFORMATION: 1-frame peptide

<400> SEQUENCE: 24

Met Gln Ala Asn Phe Leu Arg
1               5

<210> SEQ ID NO 25
<211> LENGTH: 9
<212> TYPE: PRT
<213> ORGANISM: Artificial Sequence
<220> FEATURE:
<223> OTHER INFORMATION: 0-frame peptide

<400> SEQUENCE: 25

Met Gln Ala Asn Phe Leu Gly Lys Ile
1               5

<210> SEQ ID NO 26
<211> LENGTH: 6
<212> TYPE: PRT
<213> ORGANISM: Artificial Sequence
<220> FEATURE:
<223> OTHER INFORMATION: -1FS products

<400> SEQUENCE: 26

Met Gln Ala Asn Phe Phe
1               5

<210> SEQ ID NO 27
<211> LENGTH: 6
<212> TYPE: PRT
<213> ORGANISM: Artificial Sequence
<220> FEATURE:
<223> OTHER INFORMATION: 0-frame peptide

<400> SEQUENCE: 27

Met Gln Ala Asn Phe Leu
1               5

<210> SEQ ID NO 28
<211> LENGTH: 4
<212> TYPE: PRT
<213> ORGANISM: Artificial Sequence
<220> FEATURE:
<223> OTHER INFORMATION: 0-frame peptide

<400> SEQUENCE: 28
```

```
Met Gln Ala Asn
1

<210> SEQ ID NO 29
<211> LENGTH: 7
<212> TYPE: PRT
<213> ORGANISM: Artificial Sequence
<220> FEATURE:
<223> OTHER INFORMATION: 0-frame peptides

<400> SEQUENCE: 29

Met Gln Ala Asn Phe Leu Trp
1               5

<210> SEQ ID NO 30
<211> LENGTH: 7
<212> TYPE: PRT
<213> ORGANISM: Artificial Sequence
<220> FEATURE:
<223> OTHER INFORMATION: 1-frame peptides

<400> SEQUENCE: 30

Met Gln Ala Asn Phe Phe Met
1               5

<210> SEQ ID NO 31
<211> LENGTH: 7
<212> TYPE: PRT
<213> ORGANISM: Artificial Sequence
<220> FEATURE:
<223> OTHER INFORMATION: 0-frame peptide

<400> SEQUENCE: 31

Met Gln Ala Asn Phe Leu Met
1               5

<210> SEQ ID NO 32
<211> LENGTH: 6
<212> TYPE: PRT
<213> ORGANISM: Artificial Sequence
<220> FEATURE:
<223> OTHER INFORMATION: +1-frame peptides

<400> SEQUENCE: 32

Met Gln Ala Asn Phe Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: 0-frame peptide

<400> SEQUENCE: 33

Met Val Ala Asn Phe Leu Gly
1               5

<210> SEQ ID NO 34
<211> LENGTH: 7
<212> TYPE: PRT
<213> ORGANISM: Artificial Sequence
<220> FEATURE:
<223> OTHER INFORMATION: 1-frame peptides

<400> SEQUENCE: 34

Met Val Ala Asn Phe Leu Arg
```

-continued

```
1               5

<210> SEQ ID NO 35
<211> LENGTH: 7
<212> TYPE: PRT
<213> ORGANISM: Artificial Sequence
<220> FEATURE:
<223> OTHER INFORMATION: -2-frame peptides

<400> SEQUENCE: 35

Met Gln Ala Asn Phe Phe Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: -2-frame peptides

<400> SEQUENCE: 36

Met Gln Ala Asn Phe Leu Tyr
1               5

<210> SEQ ID NO 37
<211> LENGTH: 4
<212> TYPE: PRT
<213> ORGANISM: Artificial Sequence
<220> FEATURE:
<223> OTHER INFORMATION: tRNAs for QANF

<400> SEQUENCE: 37

Gln Ala Asn Phe
1

<210> SEQ ID NO 38
<211> LENGTH: 17
<212> TYPE: RNA
<213> ORGANISM: Artificial Sequence
<220> FEATURE:
<223> OTHER INFORMATION: Slippery site (SS1) and the putative second
     slippery site (pSS2)

<400> SEQUENCE: 38
uuuuuuaggg uuuucuu                                                17

<210> SEQ ID NO 39
<211> LENGTH: 21
<212> TYPE: RNA
<213> ORGANISM: Artificial Sequence
<220> FEATURE:
<223> OTHER INFORMATION: -1FS efficiency with the wild-type (wt) mRNA

<400> SEQUENCE: 39
augcaggcua auuuuuuagg g                                           21

<210> SEQ ID NO 40
<211> LENGTH: 21
<212> TYPE: RNA
<213> ORGANISM: Artificial Sequence
<220> FEATURE:
<223> OTHER INFORMATION: model mRNA and peptides synthesized in all
     frames

<400> SEQUENCE: 40
augcaggcua auuuuuuaug g                                           21
```

```
<210> SEQ ID NO 41
<211> LENGTH: 4
<212> TYPE: PRT
<213> ORGANISM: Artificial Sequence
<220> FEATURE:
<223> OTHER INFORMATION: [14C]-labeled Tyr, Met, Leu or Trp

<400> SEQUENCE: 41

Leu Met Trp Tyr
1

<210> SEQ ID NO 42
<211> LENGTH: 46
<212> TYPE: RNA
<213> ORGANISM: Artificial Sequence
<220> FEATURE:
<223> OTHER INFORMATION: potential stem-loop element downstream of the
      pSS2 (pSL2)

<400> SEQUENCE: 42
augaaagauu guacugagag acaggcuaau uuuuuagggu uuucuu                          46

<210> SEQ ID NO 43
<211> LENGTH: 9
<212> TYPE: PRT
<213> ORGANISM: Artificial Sequence
<220> FEATURE:
<223> OTHER INFORMATION: -1-frame FLS

<400> SEQUENCE: 43

Met Ser Lys Ser Phe Leu Ser Ala Thr
1               5

<210> SEQ ID NO 44
<211> LENGTH: 9
<212> TYPE: PRT
<213> ORGANISM: Artificial Sequence
<220> FEATURE:
<223> OTHER INFORMATION: -1-frame FFS

<400> SEQUENCE: 44

Met Ser Lys Ser Phe Phe Ser Ala Thr
1               5

<210> SEQ ID NO 45
<211> LENGTH: 7
<212> TYPE: PRT
<213> ORGANISM: Artificial Sequence
<220> FEATURE:
<223> OTHER INFORMATION: 0-frame peptide

<400> SEQUENCE: 45

Met Ser Lys Ser Phe Leu Val
1               5

<210> SEQ ID NO 46
<211> LENGTH: 36
<212> TYPE: RNA
<213> ORGANISM: Artificial Sequence
<220> FEATURE:
<223> OTHER INFORMATION: start codon AUG

<400> SEQUENCE: 46
augagcaagu cuuuuuuagu gcuacugagc cucggg                                     36

<210> SEQ ID NO 47
```

-continued

```
<211> LENGTH: 7
<212> TYPE: PRT
<213> ORGANISM: Artificial Sequence
<220> FEATURE:
<223> OTHER INFORMATION: FFS peptide

<400> SEQUENCE: 47

Met Ser Lys Ser Phe Phe Ser
1               5

<210> SEQ ID NO 48
<211> LENGTH: 5
<212> TYPE: PRT
<213> ORGANISM: Artificial Sequence
<220> FEATURE:
<223> OTHER INFORMATION: FFS peptide

<400> SEQUENCE: 48

Met Ser Lys Ser Phe
1               5

<210> SEQ ID NO 49
<211> LENGTH: 7
<212> TYPE: PRT
<213> ORGANISM: Artificial Sequence
<220> FEATURE:
<223> OTHER INFORMATION: -2-frame peptides
<220> FEATURE:
<221> NAME/KEY: VARIANT
<222> LOCATION: (6)..(6)
<223> OTHER INFORMATION: Xaa can be Phe or Leu

<400> SEQUENCE: 49

Met Gln Ala Asn Phe Xaa Tyr
1               5

<210> SEQ ID NO 50
<211> LENGTH: 7
<212> TYPE: PRT
<213> ORGANISM: Artificial Sequence
<220> FEATURE:
<223> OTHER INFORMATION: -1-frame peptides
<220> FEATURE:
<221> NAME/KEY: VARIANT
<222> LOCATION: (6)..(6)
<223> OTHER INFORMATION: Xaa can be Phe or Leu

<400> SEQUENCE: 50

Met Gln Ala Asn Phe Xaa Met
1               5
```